(12) United States Patent
Conde et al.

(10) Patent No.: US 7,368,566 B2
(45) Date of Patent: May 6, 2008

(54) PROCESS AND INTERMEDIATES FOR PREPARING BENZAZEPINES

(75) Inventors: Jose J. Conde, King of Prussia, PA (US); Lewilynn L. Goldfinger, Collegeville, PA (US); Michael A. McGuire, King of Prussia, PA (US); Susan C. Shilcrat, King of Prussia, PA (US); Michael D. Wallace, King of Prussia, PA (US); Marvin Sungwhan Yu, Pittsburgh, PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 242 days.

(21) Appl. No.: 10/551,710

(22) PCT Filed: Mar. 29, 2004

(86) PCT No.: PCT/US2004/009909

§ 371 (c)(1),
(2), (4) Date: Oct. 3, 2005

(87) PCT Pub. No.: WO2004/089890

PCT Pub. Date: Oct. 21, 2004

(65) Prior Publication Data

US 2006/0194786 A1    Aug. 31, 2006

(51) Int. Cl.
*C07C 261/00* (2006.01)
*C07C 69/76* (2006.01)
*C07C 59/48* (2006.01)
*C07D 223/16* (2006.01)

(52) U.S. Cl. .................. 540/524; 560/29; 560/53; 560/54; 560/60; 562/470

(58) Field of Classification Search ............. 560/29, 560/53, 54, 60; 562/470; 540/524
See application file for complete search history.

(56) References Cited

U.S. PATENT DOCUMENTS

| 4,080,450 A | 3/1978 | Croisier et al. ............. 424/244 |
| 4,691,037 A | 9/1987 | Yoshikawa et al. ........... 556/18 |
| 4,939,288 A | 7/1990 | Talley ........................ 560/81 |
| 5,202,473 A | 4/1993 | Chan et al. ................. 562/496 |
| 5,508,435 A | 4/1996 | Armstrong, III et al. ... 548/543 |
| 5,596,113 A | 1/1997 | Douglas et al. ................ 556/14 |
| 5,939,412 A | 8/1999 | Bondinell et al. ........... 514/213 |
| 6,576,643 B2 | 6/2003 | Bondinell et al. ........... 514/310 |
| 6,825,188 B2 | 11/2004 | Callahan et al. ........ 514/212.07 |
| 2002/0032187 A1 | 3/2002 | Drake .................... 514/211.06 |
| 2002/0147334 A1 | 10/2002 | Miller et al. ................ 540/553 |

FOREIGN PATENT DOCUMENTS

| JP | 10130175 | 10/1996 |
| WO | WO 99/15178 | 4/1999 |
| WO | WO 00/63186 | 10/2000 |

OTHER PUBLICATIONS

Miller et al. (J. Med. Chem. 2000, 43, 22-26).*
Morimoto et al. *Tet. Letters*, 30: 735-738 (1989).
Cabri et al. *Acc. Chem. Res.*, 28: 2-7 (1995).
De Meijere et al. *Angew. Chem. Int. Ed. Engl.*, 33: 2379-2411 (1994).
McGuire et al. *Tet. Letters*, 40(17): 3293-3296 (1999).
White et al. *J. Org. Chem.*, 62: 5250-5251 (1997).
DiMichele et al. *Tetrahedron: Asymmetry*, 14: 3427-3429 (2003).
Wallace et al. *Org. Process Res. & Dev.*, 8: 738-743 (2004).
Leitner et al. *J. Am. Chem. Soc.*, 115(1): 152-159 (1993).
Saburi et al. *J. Organomet. Chem.*, 428(1-2): 155-167 (1992).
Ito et al. *Tetrahedron Lett.*, 31(19):2731-2734 (1990).
Kawano et al. *Tetrahedron Lett.*, 28(17): 1905-1908 (1987).
Mathey et al. *J. Organomet. Chem.*, 557(1): 117-120 (1998).
Shao et al. *J. Chem. Soc. Perkin Trans.*, 1(5): 1441-1445 (1990).
Shao et al. *J. Organomet. Chem.*, 435(1-2): 133-147 (1992).
Kawano et al. *J. Chem. Soc. Perkin Trans.*, 1: 1571-1575 (1989).
Miller et al. *J.Med. Chem.*, 43(1): 22-26 (2000).

* cited by examiner

Primary Examiner—Bruck Kifle
(74) *Attorney, Agent, or Firm*—Kathryn L. Sieburth; Mary E. McCarthy; Charles M. Kinzig

(57) ABSTRACT

Disclosed is a new process and intermediates for preparing benzazepines of Formula (I):

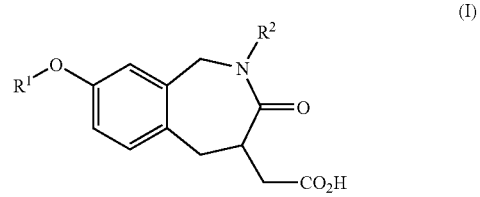

wherein $R^1$ and $R^2$ are as defined herein.

20 Claims, No Drawings

PROCESS AND INTERMEDIATES FOR PREPARING BENZAZEPINES

This application is a 371 of International Application No. PCT/US2004/009909, filed 29 Mar. 2004.

FIELD OF THE INVENTION

This invention relates to processes and intermediates for preparing benzazepine compounds that function as vitronectin receptor inhibitors.

BACKGROUND OF THE INVENTION

Integrins are a superfamily of cell adhesion receptors, which are transmembrane glycoproteins expressed on a variety of cells. These cell surface adhesion receptors include gpIIb/IIIa (the fibrinogen receptor) and $\alpha_v\beta_3$ (the vitronectin receptor). The fibrinogen receptor gpIIb/IIIa is expressed on the platelet surface, and mediates. The vitronectin receptor is known to refer to three different integrins, designated $\alpha_v\beta_1$, $\alpha_v\beta_3$ and $\alpha_v\beta_5$ Compounds that inhibit the activity of these receptors and associated integrins may be useful for the treatment of inflammation, cancer and cardiovascular disorders, such as atherosclerosis and restenosis, and diseases wherein bone resorption is a factor, such as osteoporosis. Benzazepine compounds that are potent inhibitors of the $\alpha_v\beta_3$ and $\alpha_v\beta_5$ receptors are described in U.S. Pat. Nos. 5,939,412 and 6,127,359.

Each of the above publications describes a variety of procedures for constructing benzazepines, however these processes employ expensive reagents and generally require a large number of steps in the synthetic sequence. Accordingly, it would be useful to develop an efficient and cost-effective process for the preparation of benzazepine compounds.

SUMMARY OF THE INVENTION

This invention is directed to a process for preparing a benzazepine of Formula (I):

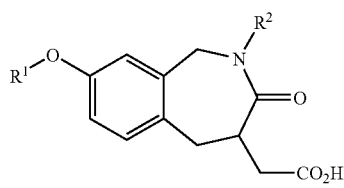

from a benzazepine-phenol of Formula (II):

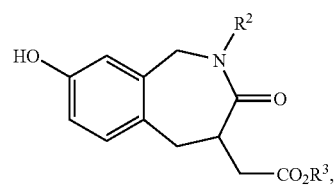

wherein the benzazepine-phenol of Formula (II) is prepared by a process comprising converting a compound of Formula (III):

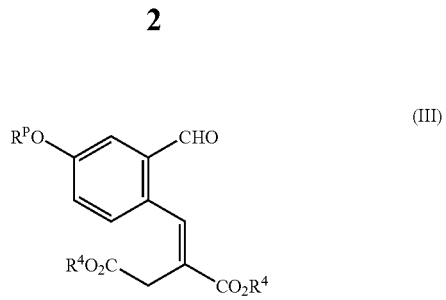

to a compound of Formula (IV):

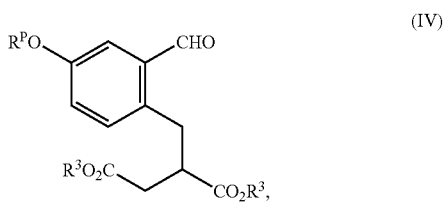

wherein $R^P$, $R^1$, $R^2$, $R^3$ and $R^4$ are as defined herein.

This process further comprises converting the compound of Formula (IV) to the compound of Formula (II).

Another aspect of this invention relates to a process for the stereospecific preparation of a benzazepine of Formula (I-S):

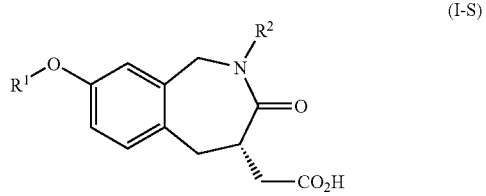

from a benzazepine-phenol of Formula (II-S):

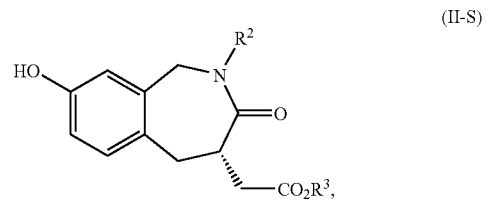

wherein the benzazepine-phenol of Formula (II-S) is prepared by a process comprising converting a compound of Formula (III):

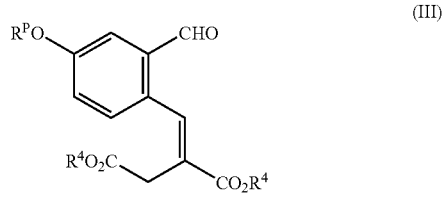

to a compound of Formula (IV-S):

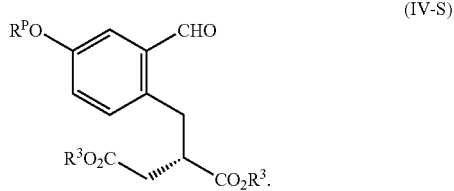

(IV-S)

This process further comprises converting the compound of Formula (IV-S) to the compound of Formula (II-S).

Another aspect of this invention is a process for the preparation of each of 8-[2-[6-(methylamino)pyridin-2-yl]-1-ethoxy]-3-oxo-2-(2,2,2-trifluoroethyl)-1,2,4,5-tetrahydro-2-benzazepine-4-acetic acid, S-(−)-8-[2-[6(methylamino) pyridin-2-yl]-1-ethoxy]-3-oxo-2-(2,2,2-trifluoroethyl)-1,2, 4,5-tetrahydro-2-benzazepine-4-acetic acid, 2,3,4,5-tetrahydro-3-oxo-8-[3-(2-pyridinylamino)propoxy]-2-(2,2, 2-trifluoroethyl)-1H-2-benzazepine-4-acetic acid, and (S)-2, 3,4,5-tetrahydro-3-oxo-8-[3-(2-pyridinylamino)propoxy]-2-(2,2,2-trifluoroethyl)-1H-2-benzazepine-4-acetic acid. Yet another aspect of this invention includes each of the compounds: methyl 2,3,4,5-tetrahydro-8-hydroxy-3-oxo-2-(2,2, 2-trifluoroethyl)-1H-2-benzazepineacetate, (S)-methyl 2,3, 4,5-tetrahydro-8-hydroxy-3-oxo-2-(2,2,2-trifluoroethyl)-1H-2-benzazepine-4-acetate, 2-[(2-formyl-4-hydroxyphenyl)methylidene]succinic acid, 2-carboxyl-4-[(2-formyldimethylacetal-4-hydroxyphenyl)]butyric acid, bis(dicyclohexylamine) salt, (S)-2-carboxyl-4[(2-formyldimethylacetal-4-hydroxyphenyl)]butyric acid, bis (dicyclohexylamine) salt, dimethyl 2-[(2-formylhydroxyphenyl)methyl]butanedioate, and dimethyl (2S)-2-[(2-formyl-4-hydroxyphenyl)methyl]butanedioate, and the process for the preparation thereof.

DETAILED DESCRIPTION OF THE INVENTION

Benzazepine compounds that may be prepared by the processes of this invention include the compounds of Formula (I) and Formula (I-S):

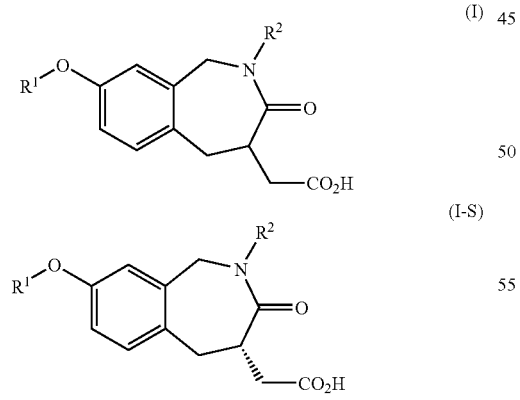

wherein:

$R^2$ is $R^7$, $C_1$-$C_4$ alkyl, $C_1$-$C_4$ haloalkyl, A-$C_0$-$C_4$ alkyl-, A-$C_2$-$C_4$ alkenyl-, A-$C_2$-$C_4$ alkynyl-, A-$C_3$-$C_4$ oxoalkenyl-, A-$C_3$-$C_4$ oxoalkynyl-, A-$C_0$-$C_4$ aminoalkyl-, A-$C_3$-$C_4$ aminoalkenyl-, A-$C_3$-$C_4$ aminoalkynyl-, optionally substituted by any accessible combination of one or more of $R^{10}$ or $R^7$;

A is H, $C_3$-$C_6$ cycloalkyl, Het or Ar;

$R^7$ is —$COR^8$, —$COCR'_2R^9$, —$C(S)R^8$, —$S(O)_mOR'$, —$S(O)_mNR'R''$, —$PO(OR')$, —$PO(OR')_2$, —$NO_2$, or tetrazolyl;

each $R^8$ independently is —$OR'$, —$NR'R''$, —$NR'SO_2R'$, —$NR'OR'$, or —$OCR'_2CO(O)R'$;

$R^9$ is —$OR'$, —$CN$, —$S(O)_rR'$, —$S(O)_mNR'_2$, —$C(O)R'$, $C(O)NR'_2$, or —$CO_2R'$;

$R^{10}$ is H, halo, —$OR^{11}$, —$CN$, —$NR'R^{11}$, —$NO_2$, —$CF_3$, $CF_3S(O)_r$—, —$CO_2R'$, —$CONR'_2$, A-$C_0$-$C_6$ alkyl-, A-$C_1$-$C_6$ oxoalkyl-, A-$C_2$-$C_6$ alkenyl-, A-$C_2$-$C_6$ alkynyl-, A-$C_0$-$C_6$ alkyloxy-, A-$C_0$-$C_6$ alkylamino- or A-$C_0$-$C_6$ alkyl-$S(O)_r$—;

$R^{11}$ is $R'$, —$C(O)R'$, —$C(O)NR'_2$, —$C(O)OR'$, —$S(O)_m R'$, or —$S(O)_mNR'_2$;

$R^1$ is

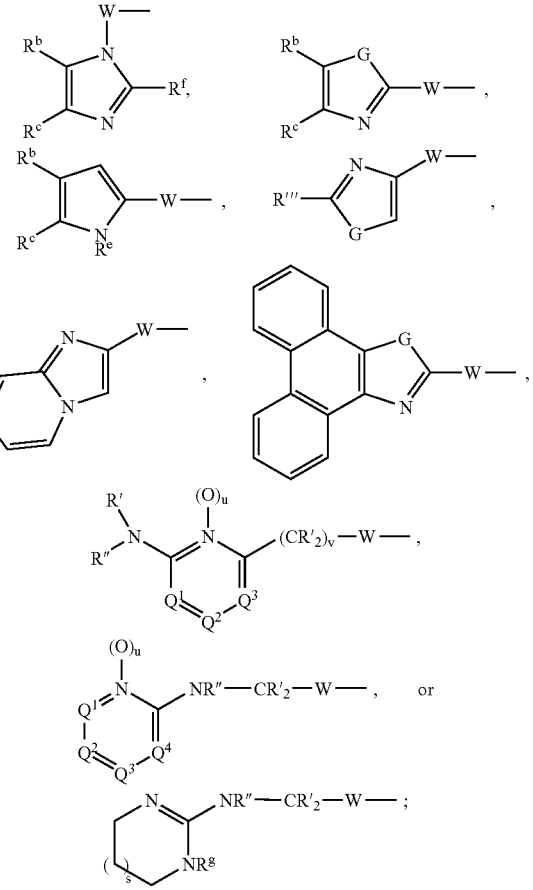

W is —$(CHR^g)_a$—U—$(CHR^g)_b$—;

U is absent or CO, $CR^g_2$, $C(=CR^g_2)$, $S(O)_k$, O, $NR^g$, $CR^gOR^g$, $CR^g(OR^k)CR^g_2$, $CR^g_2CR^g(OR^k)$, $C(O)CR^g_2$, $CR^g_2C(O)$, $CONR^i$, $NR^iCO$, $OC(O)$, $C(O)O$, $C(S)O$, $OC(S)$, $C(S)NR^g$, $NR^gC(S)$, $S(O)_2NR^g$, $NR^gS(O)_2N=N$, $NR^gNR^g$, $NR^gCR^g_2$, $CR^g_2NR^g$, $CR^g_2O$, $OCR^g_2$, $C\equiv C$ or $CR^g=CR^g$;

G is $NR^e$, S or O;

$R^g$ is H, $C_1$-$C_6$ alkyl, Het-$C_0$-$C_6$ alkyl, $C_3$-$C_7$ cycloalkyl-$C_0$-$C_6$ alkyl or Ar—$C_0$-$C_6$ alkyl;

$R^k$ is $R^g$, —$C(O)R^g$, or —$C(O)OR^f$;

$R^i$ is H, $C_1$-$C_6$ alkyl, Het-$C_0$-$C_6$ alkyl, $C_3$-$C_7$ cycloalkyl-$C_0$-$C_6$ alkyl, Ar—$C_0$-$C_6$ alkyl, or $C_1$-$C_6$ alkyl substituted by one to three groups chosen from halogen, CN, $NR^g_2$, $OR^g$, $SR^g$, $CO_2R^g$, and $CON(R^g)_2$;

$R^g$ is H, $C_1$-$C_6$ alkyl or Ar—$C_0$-$C_6$ alkyl;

$R^e$ is H, $C_1$-$C_6$ alkyl, Ar—$C_0$-$C_6$ alkyl, Het-$C_0$-$C_6$ alkyl, $C_3$-$C_7$ cycloalkyl-$C_0$-$C_6$ alkyl, or $(CH_2)_k CO_2 R^g$;

$R^b$ and $R^c$ are independently selected from H, $C_1$-$C_6$ alkyl, Ar—$C_0$-$C_6$ alkyl, Het-$C_0$-$C_6$ alkyl, or $C_3$-$C_6$ cycloalkyl-$C_0$-$C_6$ alkyl, halogen, $CF_3$, $OR^f$, $S(O)_k R^f$, $COR^f$, $NO_2$, $N(R^f)_2$, $CO(NR^f)_2$, $CH_2N(R^f)_2$, or $R^b$ and $R^c$ are joined together to form a five or six membered aromatic or non-aromatic carbocyclic or heterocyclic ring, optionally substituted by up to three substituents chosen from halogen, $CF_3$, $C_1$-$C_4$ alkyl, $OR^f$, $S(O)_k R^f$, $COR^f$, $CO_2 R^f$, OH, $NO_2$, $N(R^f)_2$, $CO(NR^f)_2$, and $CH_2N(R^f)_2$; or methylenedioxy;

$Q^1$, $Q^2$, $Q^3$ and $Q^4$ are independently N or C—$R^y$, provided that no more than one of $Q^1$, $Q^2$, $Q^3$ and $Q^4$ is N;

R' is H, $C_1$-$C_6$ alkyl, Ar—$C_0$-$C_6$ alkyl or $C_3$-$C_6$ cycloalkyl-$C_0$-$C_6$ alkyl;

R" is R', —C(O)R' or —C(O)OR';

R''' is H, $C_1$-$C_6$ alkyl, Ar—$C_0$-$C_6$ alkyl, Het-$C_0$-$C_6$ alkyl, or $C_3$-$C_6$ cycloalkyl-$C_0$-$C_6$ alkyl, halogen, $CF_3$, $OR^f$, $S(O)_k R^f$, $COR^f$, $NO_2$, $N(R^f)_2$, $CO(NR^f)_2$, $CH_2N(R^f)_2$;

$R^y$ is H, halo, —$OR^g$, —$SR^g$, —CN, —$NR^g R^k$, —$NO_2$, —$CF_3$, $CF_3 S(O)_r$—, —$CO_2 R^g$, —$COR^g$ or —$CONR^g_2$, or $C_1$-$C_6$ alkyl optionally substituted by halo, —$OR^g$, —$SR^9$, —CN, —$NR^g R"$, —$NO_2$, —$CF_3$, R'$S(O)_r$—, —$CO_2 R^g$, —$COR^g$ or —$CONR^g_2$;

a is 0, 1 or 2;
b is 0, 1 or 2;
k is 0, 1 or 2;
m is 1 or 2;
r is 0, 1 or 2;
s is 0, 1 or 2;
u is 0 or 1; and
v is 0 or 1;

or a pharmaceutically acceptable salt thereof.

As used herein, $C_1$-$C_4$ alkyl as applied herein means an optionally substituted alkyl group of 1 to 4 carbon atoms, and includes methyl, ethyl, n-propyl, isopropyl, n-butyl, isobutyl and t-butyl. $C_1$-$C_6$ Alkyl additionally includes pentyl, n-pentyl, isopentyl, neopentyl and hexyl and the simple aliphatic isomers thereof. $C_0$-$C_4$ Alkyl and $C_0$-$C_6$ alkyl additionally indicates that no alkyl group need be present (e.g., that a covalent bond is present).

Any $C_1$-$C_4$ alkyl or $C_1$-$C_6$ alkyl, $C_2$-$C_6$ alkenyl, $C_2$-$C_6$ alkynyl or $C_1$-$C_6$ oxoalkyl may be optionally substituted with the group $R^x$, which may be on any carbon atom that results in a stable structure and is available by conventional synthetic techniques. Suitable groups for $R^x$ are $C_1$-$C_4$ alkyl, OR', SR', $C_1$-$C_4$ alkylsulfonyl, $C_1$-$C_4$ alkylsulfoxyl, —CN, $N(R')_2$, $CH_2N(R')_2$, —$NO_2$, —$CF_3$, —$CO_2 R'$—$CON(R')_2$, —COR', —NR'C(O)R', F, Cl, Br, I, or $CF_3 S(O)_r$—, wherein r is 0, 1 or 2.

Halogen or halo means F, Cl, Br, and I.

Ar, or aryl, as applied herein, means phenyl or naphthyl, or phenyl or naphthyl substituted by one to three substituents, such as those defined above for alkyl, especially $C_1$-$C_4$ alkyl, $C_1$-$C_4$ alkoxy, $C_1$-$C_4$ alkylthio, $CF_3$, $NH_2$, OH, F, Cl, Br or I.

Het, or heterocycle, indicates an optionally substituted five or six membered monocyclic ring, or a nine or ten-membered bicyclic ring containing one to three heteroatoms chosen from the group of nitrogen, oxygen and sulfur, which are stable and available by conventional chemical synthesis. Illustrative heterocycles are benzofuryl, benzimidazolyl, benzopyranyl, benzothienyl, furanyl, imidazolyl, indolyl, morpholinyl, piperidinyl, piperazinyl, pyrrolyl, pyrrolidinyl, tetrahydropyridinyl, pyridinyl, thiazolyl, thienyl, quinolyl, isoquinolyl, and tetra- and perhydro-quinolyl and isoquinolyl. Any accessible combination of up to three substituents on the Het ring, such as those defined above for alkyl that are available by chemical synthesis and are stable are within the scope of this invention.

$C_3$-$C_7$ Cycloalkyl refers to an optionally substituted carbocyclic system of three to seven carbon atoms, which may contain up to two unsaturated carbon-carbon bonds. Typical of $C_3$-$C_7$ cycloalkyl are cyclopropyl, cyclobutyl, cyclopentyl, cyclopentenyl, cyclohexyl, cyclohexenyl and cycloheptyl. Any combination of up to three substituents, such as those defined above for alkyl, on the cycloalkyl ring that is available by conventional chemical synthesis and is stable, is within the scope of this invention.

When $R^b$ and $R^c$ are joined together to form a five- or six-membered aromatic or non-aromatic carbocyclic or heterocyclic ring fused to the ring to which $R^b$ and $R^c$ are attached, the ring formed will generally be a five- or six-membered heterocycle selected from those listed above for Het, or will be a phenyl, cyclohexyl or cyclopentyl ring. Preferably $R^b$ and $R^c$ will be –D1=D2-D3=D4 wherein D1-D4 are independently CH, N or C—$R^x$ with the proviso that no more than two of D1-D4 are N. Most preferably, when $R^b$ and $R^c$ are joined together they form the group —CH=CH—CH=CH—.

Compounds of Formula (I) may be prepared by a process comprising converting a compound of Formula (III):

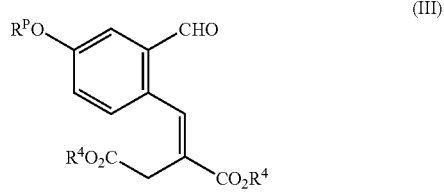

to a compound of Formula (IV):

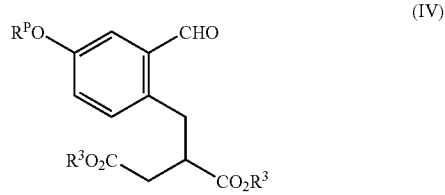

wherein $R^P$ is H or a suitable phenol protecting group, $R^3$ and $R^4$ are the same or different and are each independently H or a carboxylic acid ester protecting group. As described herein, this conversion may be conducted by hydrogenation, specifically catalytic hydrogenation. It will be understood by those skilled in the art that different reaction conditions (hydrogen pressure, catalyst, temperature, solvent, etc.) may be required to effect this conversion when different protecting groups are used. Additionally, the use of different protecting groups can result in different, often poorer, conversion yields. In another embodiment, each $R^3$ and $R^4$ may be independently H, $C_1$-$C_6$ alkyl or phenyl $C_1$-$C_4$ alkyl- (e.g., benzyl) wherein the phenyl moiety may be unsubstituted or substituted by one or more substituents selected from ortho and para substituents selected from chloro, bromo, nitro, methoxy and methyl. In a specific embodiment, the process of this invention is conducted wherein $R^3$ and $R^4$ are each independently H or $C_1$-$C_4$ alkyl, specifically $R^3$ is methyl and $R^4$ is H. The term "$R^P$" is used herein to denote H or a suitable protecting group for a phenolic functional group. In one specific embodiment of this invention, $R^P$ of compounds III, IV and IV-S is H.

Suitable protecting groups for phenols, amines, carboxylic acids, aldehydes, etc., and the methods for protecting and de-protecting such substituents using such suitable protecting groups are well known to those skilled in the art; examples of which may be found in T. Greene and P. Wuts, *Protecting Groups in Chemical Synthesis* (3rd ed.), John Wiley & Sons, NY (1999). For example, suitable phenol protecting groups include benzyloxycarbonyl, benzyl, and the like. Substitution of the benzyloxycarbonyl or benzyl protecting groups can be used to modify the reactivity of the protective group. Suitable substitution of the phenyl ring moiety of the benzyloxycarbonyl or benzyl group is ortho and/or para substitution with chloro, bromo, nitro, methoxy or methyl. Suitable amine protecting groups include benzyl, Boc, Cbz, phthaloyl, Fmoc and the like. Suitable carboxylic acid ester protecting groups (e.g., $R^3$ or $R^4$) include methyl, ethyl, t-Bu, cHex, benzyl, substituted benzyl, (pivaloyl)methyl or (2-methyl-2-methoxypropanoyl)methyl esters and the like. Suitable aldehyde protecting groups (represented hereinbelow as $-ZR^5$ and $-Z'R^{5'}$) include. acetals (cyclic acetals, non-cyclic acetals (e.g., di-alkyl acetals) and aminals.

Methods for removal of carboxy or amino protecting groups are well known in the art. For example, an alkyl or cycloalkyl ester may be removed by basic hydrolysis, for instance an alkali metal hydroxide, such as sodium, potassium or lithium hydroxide in a suitable solvent, such as aqueous alcohol. A benzyl ester is typically removed by hydrogenation over a palladium catalyst. A basic nitrogen protected by a tert-butyloxycarbonyl group, or a t-butyl ester, is typically removed by acid treatment, such as by trifluoroacetic acid or hydrochloric acid, optionally diluted with a solvent, such as methylene chloride and/or dioxane. The benzyloxycarbonyl group is generally removed by hydrogenation over a palladium catalyst. A trifluoroacetyl group is typically removed by basic hydrolysis, such as by treatment with an alkali metal hydroxide in a suitable solvent.

In yet another specific embodiment of this invention, a compound of Formula (I) may be prepared by a process which comprises converting a compound of Formula (III) to a compound of Formula (IV-S)

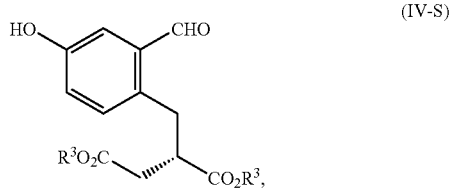

(IV-S)

wherein $R^3$ is as defined above.

According to the process of this invention, the compound of Formula (III) is converted to the compound of Formula (IV) via reduction of an intermediate compound of Formula (A) having the structure:

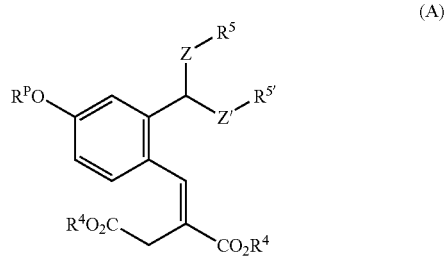

(A)

wherein $R^4$ is as defined above and the moieties $-ZR^5$ and $-Z'R^{5'}$ taken together constitute a protected aldehyde moiety (e.g., an acetal, aminal, etc.) wherein $R^5$ and $R^{5'}$ are $C_1$-$C_4$ alkyl or $R^5$ and $R^{5'}$, taken together with the atoms to which they are attached form a saturated 5- or 6-membered heterocyclic ring and Z and Z' are independently selected from O, NH or $NCH_3$. In one embodiment, the process of this invention is conducted wherein Z and Z are both O. In another embodiment, the process of this invention is conducted wherein $R^5$ and $R^{5'}$ are each $C_1$-$C_4$ alkyl, specifically methyl, $R^P$ is H and each $R^4$ is H.

The intermediate compound of Formula (A), where each $R^4$ is H. may be crystallized from the reaction mixture, specifically as a base salt. Examples of base salts of the intermediate compound of Formula (A) include the di-alkaline metal hydroxide salts (such as the di-sodium hydroxide salt, the di-potassium hydroxide salt or the di-lithium hydroxide salt) or bis-amine salts, wherein any basic mono-, di- or tri-substituted alkyl or aryl amine, or diamine (such as ethylene diamine) may be used to form the bis-salt. Useful amines include dicyclohexylamine and tert-butyl amine. In one embodiment, the compound of Formula (A) was preferably isolated as a bis(dicyclohexylamine salt).

A compound of Formula (III) is converted to a compound of Formula (A), bearing a protected aldehyde moiety using conventional procedures. The aldehyde protecting group may be removed at a suitable point in the reaction sequence of the process of this invention to provide a desired intermediate or target compound. Preferably, the aldehyde protecting groups is removed after hydrogenation of the compound of Formula (A).

Reduction of a compound of Formula (A), by hydrogenation using a palladium catalyst (e.g., palladium on carbon) results in the formation of a compound of Formula (B):

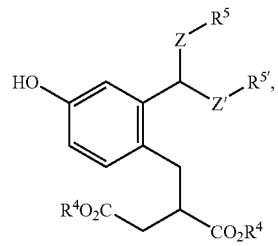

(B)

wherein Z, Z', $R^4$, $R^5$, and $R^{5'}$ are as defined above. Preferred vitronectin inhibitor compounds of Formula (I) have been identified as possessing an absolute configuration of (S) at the 4-position of the benzazepine. Accordingly, a preferred embodiment of the process of this invention comprises conducting the reduction of a compound of Formula (A) of this invention by hydrogenation using an optically active hydrogenation catalyst or by using components that form an optically active hydrogenation catalyst in situ to form a compound of Formula (B-S), substantially as (S) enantiomer:

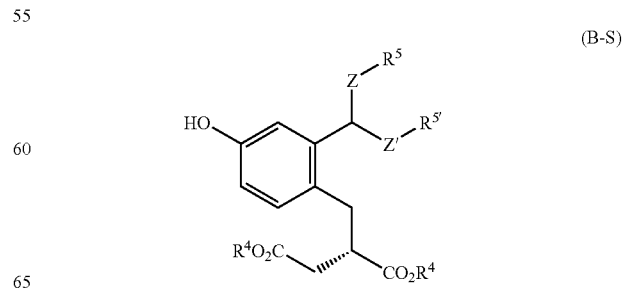

(B-S)

Asymmetric hydrogenation catalysts that may be used to provide substantially the (S)-isomer of Compound (B-S), and thereby Compounds (I-S), (II-S), (IV-S) are known in the art. See for example, U.S. Pat. No. 4,939,288, T. Morimoto, et al., *Tetrahedron Letters*, Vol. 30, No. 6, 735-738 (1989) and J. D. White, et al., *J. Org. Chem.*, Vol. 62, 5250-5251 (1997). Suitable hydrogenation catalysts include [Rh(COD)Cl]$_2$—(S,S)-DIOP, [Rh(NBD)]$_2$ClO$_4$-JOSIPHOS, [(R,R-DIPAMP)Rh(COD)]BF$_4$, [(S,S-DiethylDUPHOS)Rh]SO$_3$CF$_3$, and [Ru(S-BINAP)Cl]$_2$-TEA (with or without additional TEA). Preferably, the hydrogenation catalyst is [Ru(S-BINAP)Cl]$_2$-TEA (without added TEA). Preferably, the asymmetric hydrogenation is conducted in the presence of a mono-, di- or tri-substituted amine base. It will be understood by those skilled in the art that the use of different amine bases (e.g., tert-butyl amine or triethylamine or di-cyclohexylamine) will provide different reaction outcomes (% conversion/yield and % enantiomeric excess) when different protecting groups are used. The identification of preferred and/or optimal protecting group/amine base combinations is considered to be a matter of routine experimentation for one of ordinary skill in the art.

One embodiment of this invention relates to a process for the preparation of a compound of Formula (II), comprising the steps of:

1) treating a compound having Formula (a)

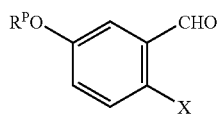
(a)

wherein $R^P$ is H or a suitable phenol protecting group and X is halogen, —OSO$_2$F, or —OSO$_2$CF$_3$, with a compound having the Formula:

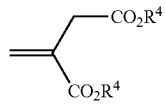

to form a compound of Formula (b)

(b)

2) converting the compound of Formula (b) to a compound of Formula (c);

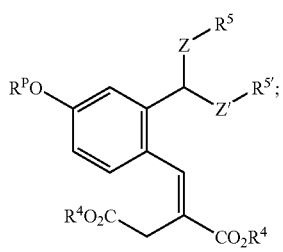
(c)

wherein Z, Z', $R^5$ and $R^{5'}$ are identified above, 3) converting the compound of Formula (c) to a compound of Formula (d):

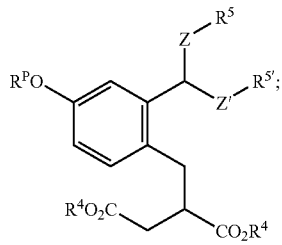
(d)

4) converting the compound of Formula (d) to a compound of Formula (e)

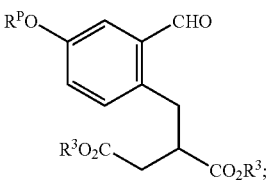
(e)

5) converting the compound of Formula (e) to a compound of Formula (f)

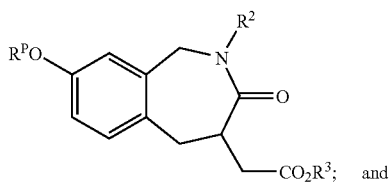
(f)

and 6) converting the compound of Formula (f) to a compound of Formula (II).

In one embodiment of the process of this invention, $R^3$ and $R^4$ are each independently H or C$_1$-C$_4$ alkyl (more specifically, $R^3$ is methyl and $R^4$ is H), $R^P$ is H, X is a halogen, Z and Z' are O and $R^5$ and $R^{5'}$ are C$_1$-C$_4$ alkyl.

Another embodiment of this invention relates to a process for the preparation of a compound of Formula II, comprising the steps of:

1) converting 3-hydroxybenzaldehyde to a compound of Formula (aa)

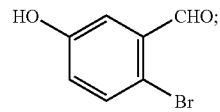
(aa)

2) treating the compound of Formula (aa) with itaconic acid to form a compound of Formula (bb):

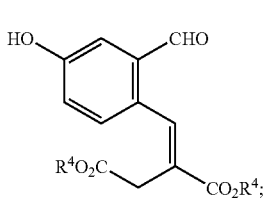
(bb)

3) converting the compound of Formula (bb) to a compound of Formula (cc)

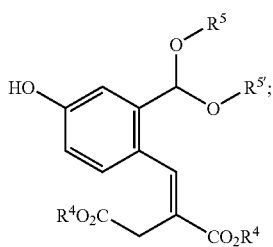
(cc)

4) converting the compound of Formula (cc) to a compound of Formula (dd)

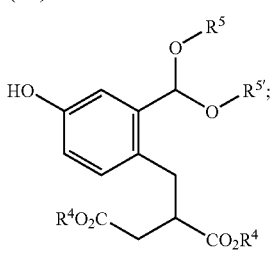
(dd)

5) converting the compound of Formula (dd) to a compound of Formula (ee)

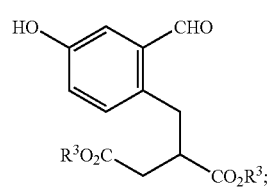
(ee)

6) converting the compound of Formula (ee) to the compound of Formula (II).

In a specific embodiment of the process of this invention described above, $R^3$ and $R^4$ are each independently H or $C_1$-$C_4$ alkyl (more specifically, $R^3$ is methyl and $R^4$ is H), $R^P$ is H, and $R^5$ and $R^{5'}$ are methyl.

Another embodiment of this invention relates to a process for the preparation of a compound of Formula (II) comprising the steps of:

1) converting a compound having Formula (a)

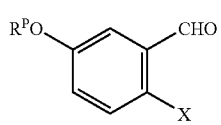
(a)

wherein $R^P$ is H or a suitable phenol protecting group and X is halogen, —$OSO_2F$, or —$OSO_2CF_3$, to a compound of Formula (a')

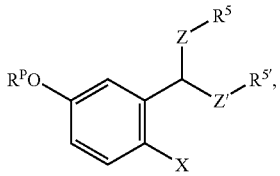
(a')

wherein —$ZR^5$ and —$Z'R^{5'}$ are as defined hereinabove;

2) treating the compound of Formula (a') with a compound having the Formula:

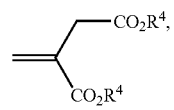

to form a compound of Formula (c')

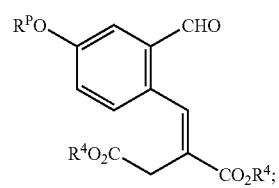
(b')

3) converting the compound of Formula (b') to a compound of Formula (c);

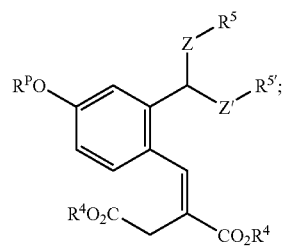
(c)

4) converting the compound of Formula (c) to a compound of Formula (d)

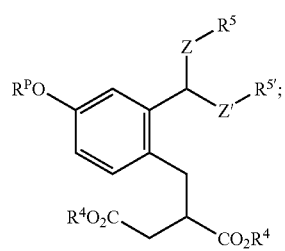
(d)

5) converting the compound of Formula (d) to a compound of Formula (e)

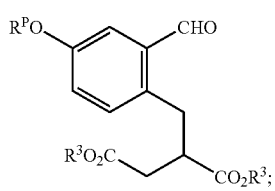
(e)

6) converting the compound of Formula (e) to a compound of Formula (f)

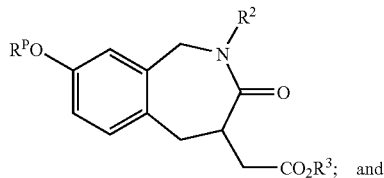
(f)

and 7) converting the compound of Formula (f) to the compound of Formula (II).

In one embodiment of the process of this invention described above, $R^3$ and $R^4$ are each independently H or $C_1$-$C_4$ alkyl (more specifically, $R^3$ is methyl and $R^4$ is H), $R^P$ is H, X is a halogen, Z and Z' are O and $R^5$ and $R^{5'}$ are $C_1$-$C_4$ alkyl.

Another embodiment of this invention relates to a process for the preparation of a compound of Formula (II) comprising the steps of:

1) converting 2-bromo-5-hydroxy-benzaldehyde to a compound of Formula (h)

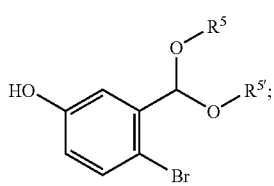
(h)

2) treating the compound of Formula (h) with itaconic acid to form a compound of Formula (i)

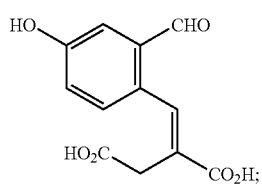
(i)

3) converting the compound of Formula (i) to a compound of Formula (j);

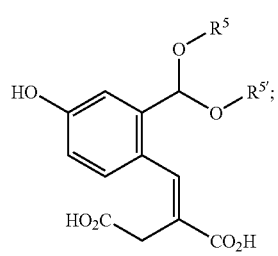
(j)

4) converting the compound of Formula (j) to a compound of Formula (k)

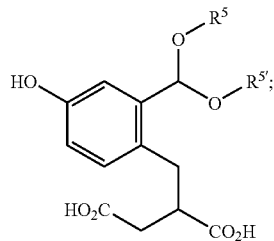
(k)

5) converting the compound of Formula (k) to a compound of Formula (l)

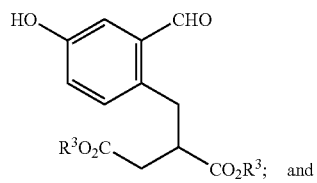
(l)

and 6) converting the compound of Formula (l) to the compound of Formula (II).

In a specific embodiment of the process of this invention described above, $R^3$ is methyl, $R^P$ is H, and $R^5$ and $R^{5'}$ are methyl.

Accordingly, in another embodiment of this invention, the process for the preparation of a compound of Formula (II-S) comprising the steps of:

1) converting the compound having the formula:

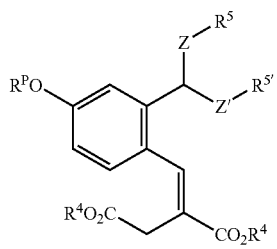

to a compound having the formula:

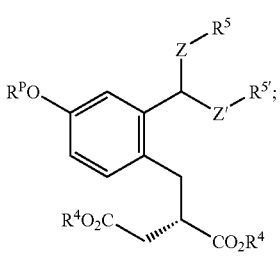

2) converting the compound formed in step 1) into a compound having the formula:

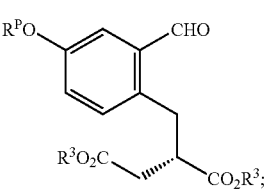

3) converting the compound formed in step 2) into the compound having the formula:

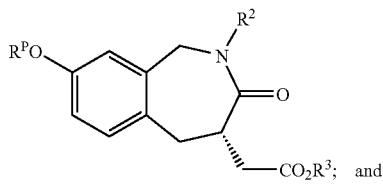

4) converting the compound formed in step 3) into the compound of Formula (II-S).

More specifically, a process for the preparation of a compound of Formula (II-S) comprising the steps of:

1) converting the compound having the formula:

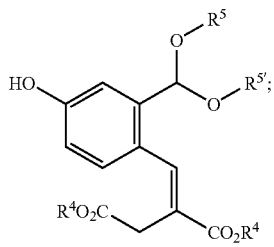

into a compound having the formula:

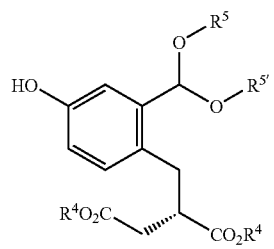

2) converting the compound formed in step 1) into a compound having the formula:

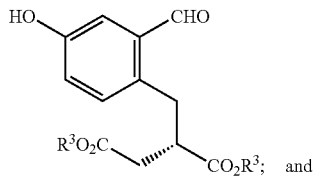

3) converting the compound formed in step 2) into the compound of Formula (II-S).

Another embodiment of this invention relates to a process for the preparation of a compound of Formula I, having the formula:

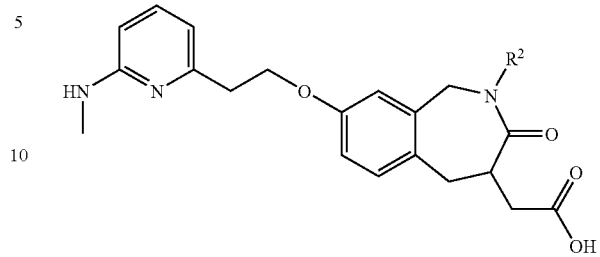

comprising the steps of:

1) converting 2-amino-6-methylpyridine into a compound having the Formula:

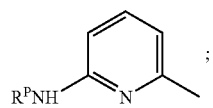

wherein $R^P$ is a suitable amino protecting group, 2) converting the compound formed in step 1) to a compound having the formula:

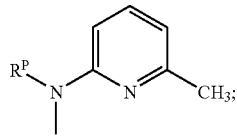

3) converting the compound formed in step 2) to a compound having the formula:

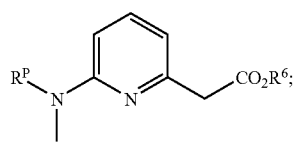

wherein $R^6$ is H or a suitable alkyl carboxylic acid ester (e.g., acetyl) protecting group;

4) converting the compound formed in step 3) to a compound having the formula:

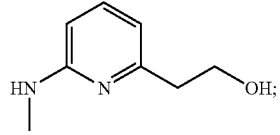

5) treating the compound formed in step 4) with a compound having the formula:

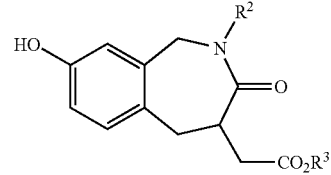

to form a compound having the formula:

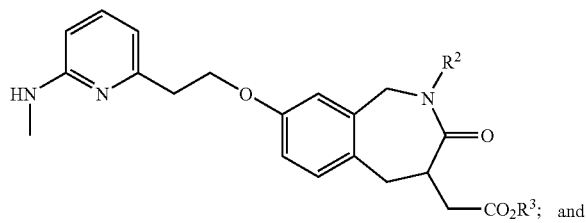

6) converting the compound formed in step 5) to the compound of Formula I.

In one embodiment of the process of this invention described above, $R^P$ is tert-butoxycarbonyl, $R^3$ is H or $C_1$-$C_4$ alkyl (more specifically, $R^3$ is methyl), and $R^6$ is $C_1$-$C_4$ alkyl.

One embodiment of this invention relates to a process for the preparation of a compound of Formula (I), having the formula:

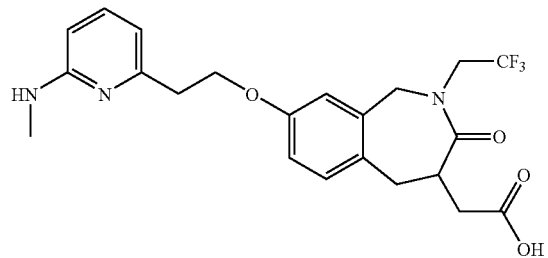

comprising the steps of:
1) converting 2-amino-6-methylpyridine into a compound having the Formula:

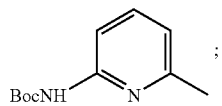

2) converting the compound formed in step 1) to a compound having the formula:

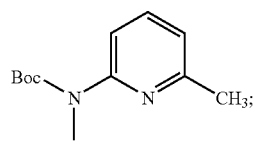

3) converting the compound formed in step 2) to a compound having the formula:

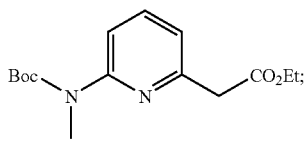

4) converting the compound formed in step 3) to a compound having the formula:

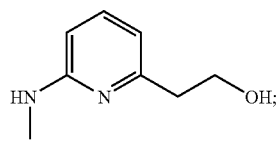

5) treating the compound formed in step 4) with a compound having the formula:

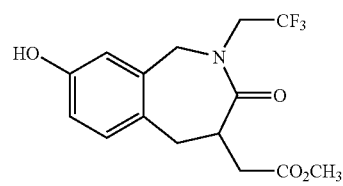

to form a compound having the formula:

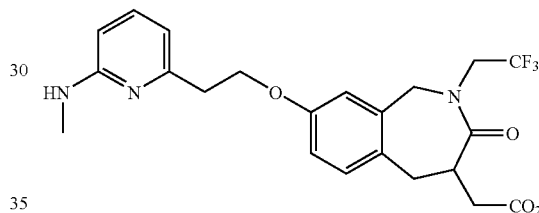

6) converting the compound formed in step 5) to the compound of Formula (I).

Another embodiment of this invention relates to a process for the preparation of a compound of Formula (I) having the formula:

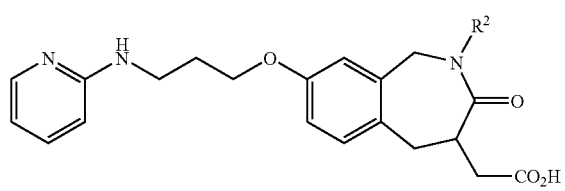

comprising the steps of:
1) converting a compound having Formula (a)

(a)

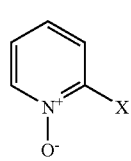

wherein X is halogen or —OSO$_2$CF$_3$, to a compound of Formula (b)

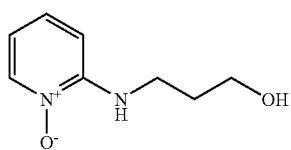

2) converting the compound formed in step 1) into a compound having the Formula:

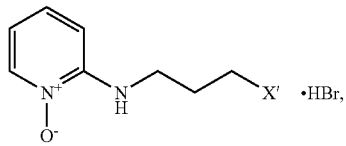

wherein X' is halogen, —OSO$_2$CH$_3$, —OSO$_2$CF$_3$, —OSO$_2$(phenyl), or —OSO$_2$(p-tolyl);

3) treating the compound formed in step 2) with a compound having the Formula:

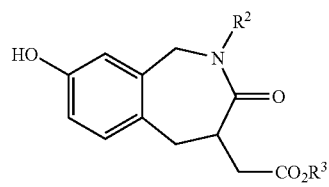

to form a compound having the formula:

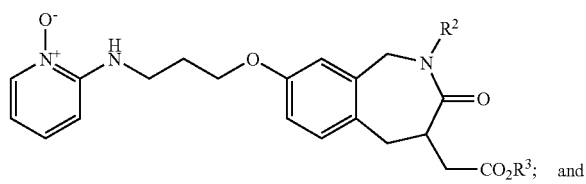

4) converting the compound formed in step 3) into the compound of Formula (I).

In one embodiment of the process of this invention described above, X and X' are each halogen and R$^3$ is C$_1$-C$_4$ alkyl, more specifically, X and X' are each bromo and R$^3$ is methyl.

Another embodiment of this invention relates to a process for the preparation of a compound of Formula (I) having the formula:

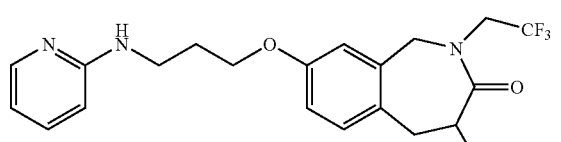

comprising the steps of:

1) converting 2-chloropyrdine, N-oxide to a compound of Formula (b)

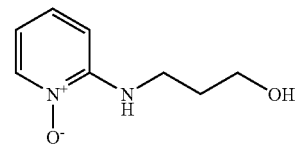

2) converting the compound formed in step 1) into a compound having the Formula:

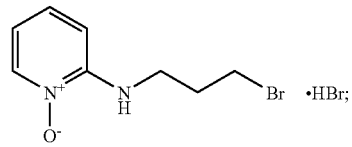

3) treating the compound formed in step 2) with a compound having the Formula:

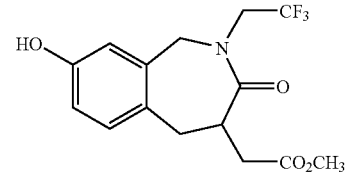

to form a compound having the formula:

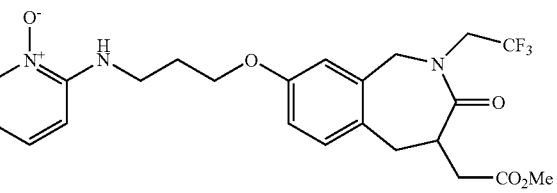

4) converting the compound formed in step 3) into the compound of Formula (I).

In another embodiment of this invention, the process for the preparation of a compound of Formula (II):

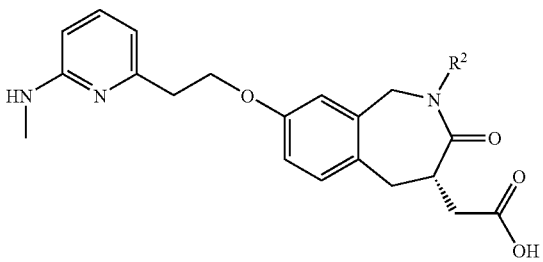

comprising the step of treating the compound having the formula:

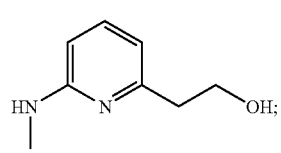

with a compound having the formula:

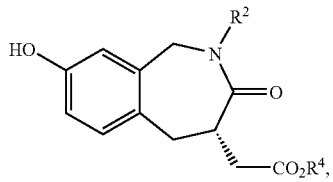

wherein $R^2$ and $R^4$ are as defined herein.

More specifically, a process for the preparation of the compound having the formula:

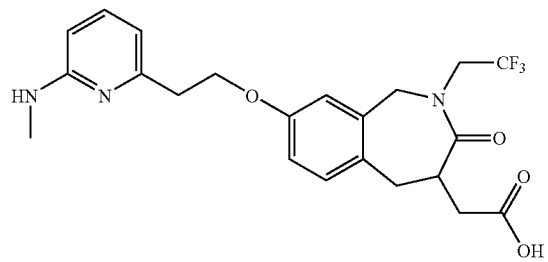

comprising the step of treating the compound having the formula:

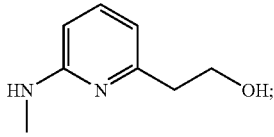

with a compound having the formula:

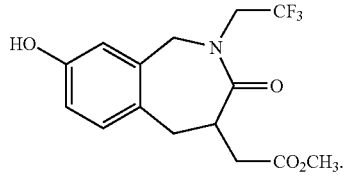

Another embodiment of this invention relates to a process for the preparation of a compound of Formula (I) having the formula:

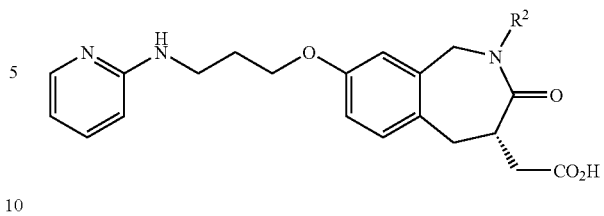

comprising the step of treating the compound having the Formula:

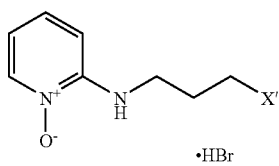

with a compound having the Formula:

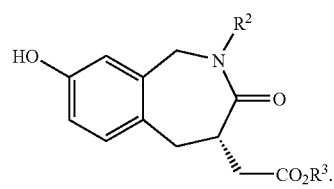

Yet another embodiment of this invention relates to a process for the preparation of a compound having the formula:

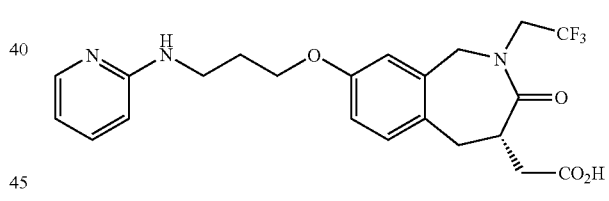

comprising the step of treating the compound having the Formula:

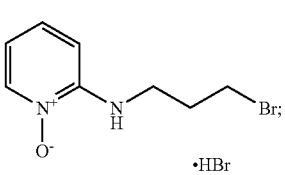

with a compound having the Formula:

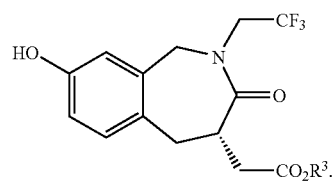

The following compound is useful in the preparation of the compounds of Formula (I) and particularly, the compounds of Formula (I-S):

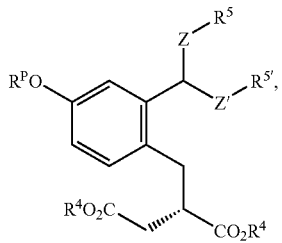

wherein $R^P$, $R^4$, $R^5$, $R^{5'}$, Z and Z' are as defined above, or a pharmaceutically acceptable salt or solvate thereof. In a more particular embodiments of the above compound of this invention, $R^4$ is H, $C_1$-$C_6$ alkyl or phenyl-$C_1$-$C_4$ alkyl-, wherein the phenyl moiety is unsubstituted or substituted by one or more substituents selected from ortho and para substituents selected from chloro, bromo, nitro, methoxy and methyl. More specifically, $R^4$ is H or $C_1$-$C_4$ alkyl, or even more specifically, $R^4$ is H. In other more specific embodiments, $R^P$ is H or Z and Z' are both O or $R^5$ and $R^{5'}$ are $C_1$-$C_4$ alkyl. More specifically, $R^5$ and $R^{5'}$ are methyl.

The following compound is also useful in the preparation of the compounds of Formula (I) and particularly, the compounds of Formula (I-S):

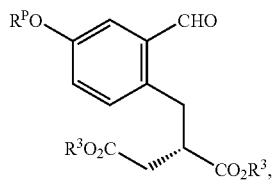

wherein $R^P$, $R^3$, $R^5$, $R^{5'}$, Z and Z' are as defined above, or a pharmaceutically acceptable salt or solvate thereof. In a more particular embodiments of the above compound of this invention, $R^3$ is H, $C_1$-$C_6$ alkyl or phenyl-$C_1$-$C_4$ alkyl-, wherein the phenyl moiety is unsubstituted or substituted by one or more substituents selected from ortho and para substituents selected from chloro, bromo, nitro, methoxy and methyl. More specifically, $R^3$ is H or $C_1$-$C_4$ alkyl. Even more specifically, $R^3$ is $C_1$-$C_4$ alkyl, specifically, methyl. In other more specific embodiments, $R^P$ is H or Z and Z' are both O or $R^5$ and $R^{5'}$ are $C_1$-$C_4$ alkyl. More specifically, $R^5$ and $R^{5'}$ are methyl.

General Methods

The following General Methods described in more detail the specific conversion steps of the above-described processes. Scheme 1 illustrates one embodiment of this invention for the preparation of a compound of Formula (II).

SCHEME 1

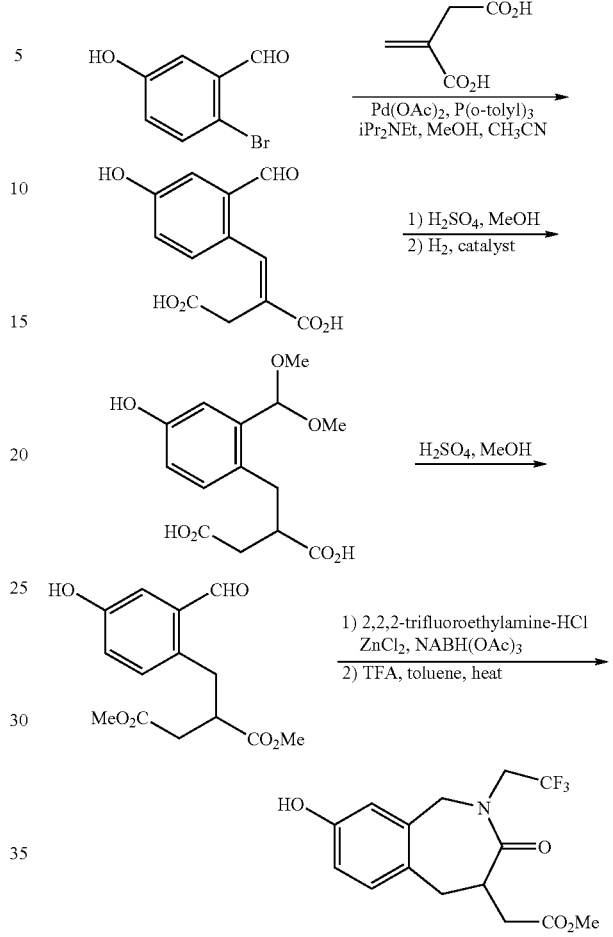

Scheme 2 illustrates one embodiment of this invention for the preparation of a compound of Formula (II).

SCHEME 2

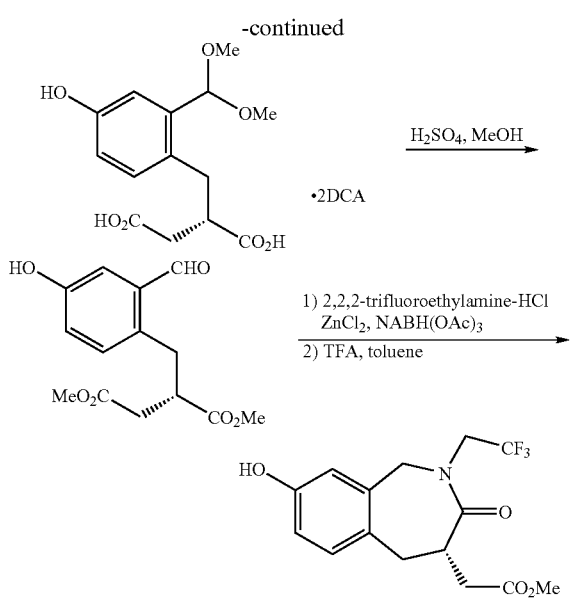

In Schemes 1 and 2, and in the processes generically described above, a 3-hydroxybenzaldehyde was brominated to provide 2-bromo-5-methoxy-benzaldehyde. This compound may be protected as an acetal in situ, then reacted with itaconic acid under Heck conditions and deprotected to provide 2-(2-formyl-4-hydroxy-benzylidene)-succinic acid. This compound was protected as an acetal and then enantioselectively hydrogenated to provide (S)-2-[2-(1,1-dimethoxy-methyl)-4-hydroxy-benzyl]-succinic acid. The asymmetric hydrogenation is preferably conducted in the presence of a mono-, di- or tri-substituted amine. Advantageously, the hydrogenation can be conduced in the presence of triethylamine or dicyclohexylamine, which provides the resulting succinic acid product as the corresponding bis-amine salt (e.g. as (S)-2-[2-(1,1-dimethoxy-methyl)-4-hydroxy-benzyl]-succinic acid bis-dicyclohexyl amine). The free acid was re-generated, the acetal was converted to an aldehyde, and the di-acid was esterified in one step to yield (S)-2-2-formyl-4-hydroxy-benzyl)-succinic acid dimethyl ester. Finally the resulting compound was reacted with 2,2,2-trifluoroethylamine under reductive amination conditions and then cyclized under acidic catalysis to provide [(S)-8-hydroxy-3-oxo-2-(2,2,2-trifluoro-ethyl)-2,3,4,5-tetrahydro-1H-benzo[c]azepin-4-yl]-acetic acid methyl ester.

Another embodiment of this invention, illustrated in Scheme 3, comprises a process for the preparation of a compound according to Formula(I) from Formula(II). Generally, this process comprises converting a benzazepine-phenol compound of Formula (II) to a benzazepione-ether compound of Formula (I) by introducing an $R^1$ substituent and hydrolyzing the carboxylate at the 4-position of the benzazepine to the corresponding acid. Suitable $R^1$ substituents are described in the patents and patent applications provided herein.

An example of an improved processes for the preparation of 8-[2-[6-(methylamino)pyridin-2-yl]-1ethoxy]-3-oxo-2-(2,2,2-trifluoroethyl)-1,2,4,5-tetrahydro-2-benzazepine-4-acetic acid, specifically, S-(−)-8-[2-[6-(methylamino)pyridin-2-yl]-1-ethoxy]-3-oxo-2-(2,2,2-trifluoroethyl)-1,2,4,5-tetrahydro-2-benzazepine-4-acetic acid using 6-(methylamino)-2-pyridineethanol is illustrated in Scheme 3.

SCHEME 3

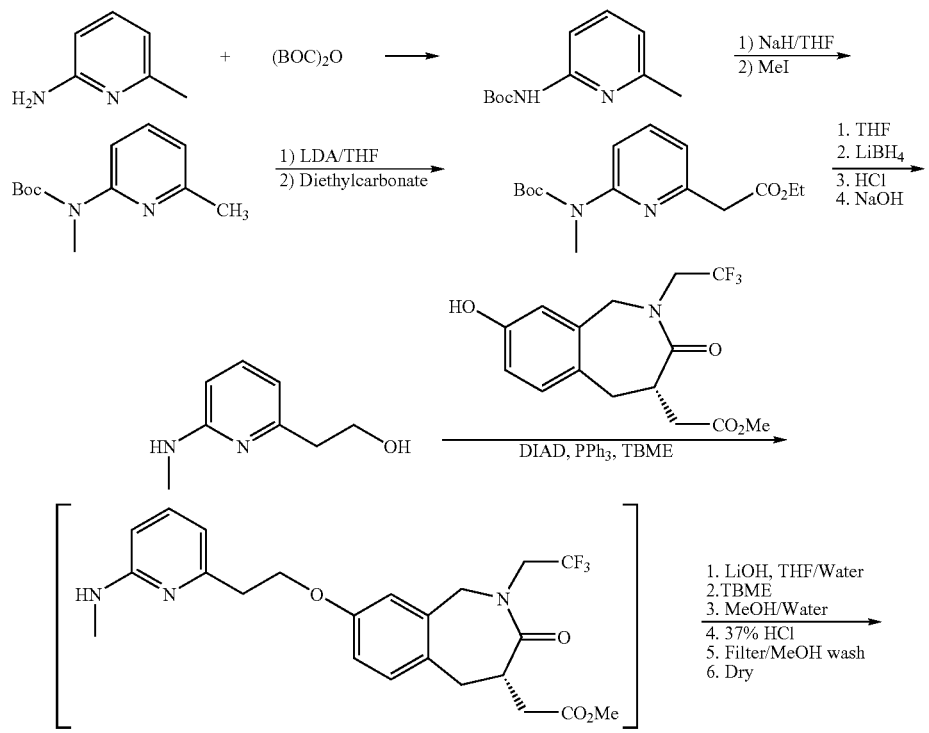

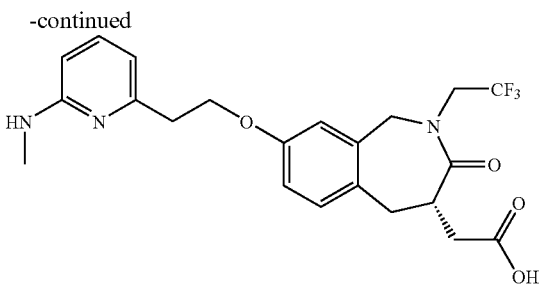

S-(−)-8-[2-[6-(Methylamino)pyridin-2-yl]-1-ethoxy]-3-oxo-2-(2,2,2-trifluoroethyl)-1,2,4,5-tetrahydro-2-benzazepine-4-acetic acid may be prepared by a thirteen step convergent synthesis from 2 key intermediates, the compound of Formula (II) or (II-S), described above and suitable $R^2$-group precursor. One such suitable $R^2$-group precursor may be prepared from 2-amino-6-methyl-pyridine as described herein. The amino group of 2-amino-6-methyl-pyridine may be was protected using any suitable protecting group. Preferably, 2-amino-6-methyl-pyridine was protected using a BOC protecting group to provide (6-methyl-pyridin-2-yl)-carbamic acid tert-butyl ester, which was converted to 1,1-dimethylethyl methyl(6-methyl-2-pyridinyl)carbamate. 1,1-Dimethylethyl methyl(6-methyl-2-pyridinyl)carbamate was converted to a 6-[[(1,1-dimethylethoxy)carbonyl]methylamino]-2-pyridineacetate by treatment with a base and a suitable carboxylating agent, where the carboxyl group may optionally be protected to provide a 6-[[(1,1-dimethylethoxy)carbonyl]methylamino]-2-pyridineacetate. In a specific embodiment of this invention, 1,1-dimethylethyl methyl(6-methyl-2-pyridinyl)carbamate was converted to ethyl 6-[[(1,1-dimethylethoxy)carbonyl]methylamino]-2-pyridineacetate by treatment with LDA and diethyl carbonate. The carboxylate moiety of the 6-[[(1,1-dimethylethoxy)carbonyl]methylamino]-2-pyridine acetate may be reduced using any suitable reducing agent to provide 2-(6-methylamino-pyridin-2-yl)-ethanol, which is a suitable pyridyl $R^2$-group precursor compound. In a specific embodiment of this invention, the 6[[(1,1-dimethylethoxy)carbonyl]methylamino]-2-pyridine acetate was reduced using lithium borohydride. Advantageously, 2-(6-methylamino-pyridin-2-yl)-ethanol may be isolated as a formate salt. The free amine may be re-generated by treatment with NaOH.

[(S)-8-Hydroxy-3-oxo-2-(2,2,2-trifluoro-ethyl)-2,3,4,5-tetrahydro-1H-benzo[c]azepin-4-yl]-acetic acid methyl ester and 2-(6methylamino-pyridin-2-yl)-ethanol may be coupled using a variety of conventional procedures, preferably using a Mitsunobo reaction. However, coupling using Williamson ether or Buchwald conditions provided low yields of coupled product or were not successful. The product (containing a —$CO_2R^3$ ester group of the compound of Formula (II) or (II-S)) may be hydrolyzed in the same step to provide crude S-(−)-8-[2-[6-(methylamino)pyridin-2-yl]-1-ethoxy]-3-oxo-2-(2,2,2-trifluoroethyl)-1,2,4,5-tetrahydro-2-benzazepine4acetic acid. The crude product is preferably recrystallized from methanol/water and the solid heated in ethyl acetate to obtain a single polymorph.

An example of an improved processes for the preparation of 2,3,4,5-tetrahydro-3-oxo-8-[3-(2-pyridinylamino)propoxy]-2-(2,2,2-trifluoroethyl)-1H-2-benzazepine-4-acetic acid, specifically, (S)-2,3,4,5-tetrahydro-3-oxo-8-[3-(2-pyridinylamino)propoxy]-2-(2,2,2-trifluoroethyl)-1H-2-benzazepine-4-acetic acid using 2-(3-bromopropyl)aminopyridine-N-oxide hydrobromide is illustrated in Scheme 4.

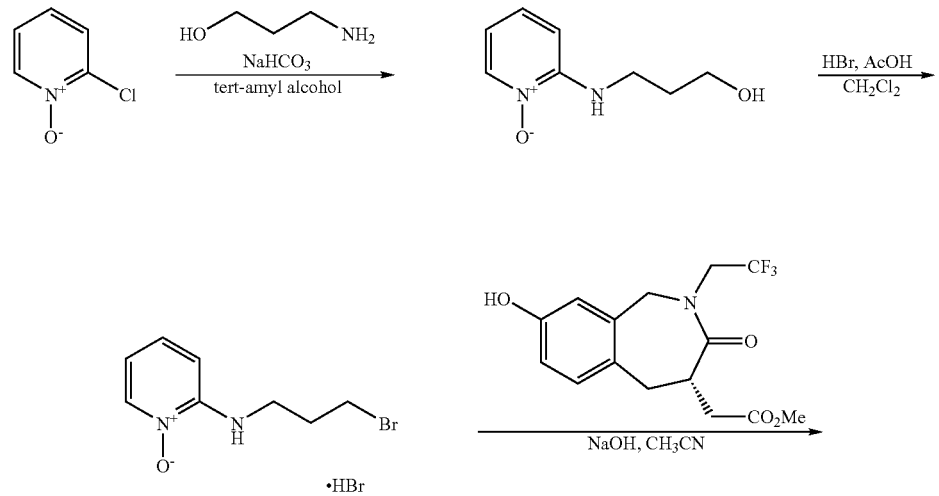

SCHEME 4

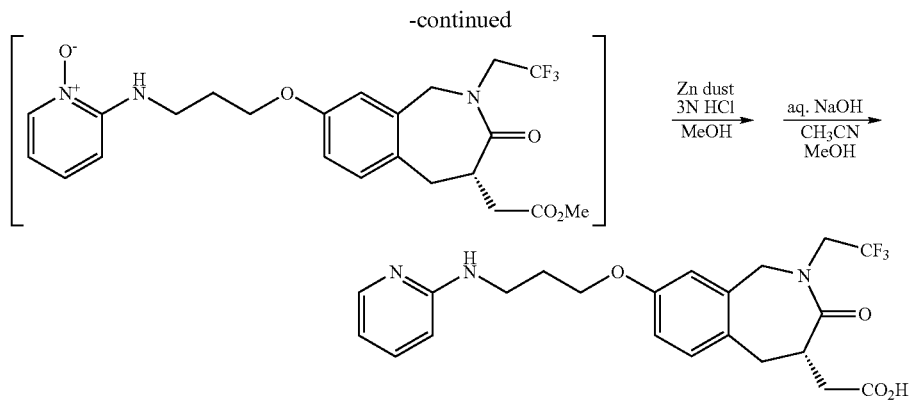

2-(3-Hydroxypropyl)aminopyridine-N-oxide may be obtained from 2-chloro-pyridine-N-oxide by treatment with sodium bicarbonate, 3-amino-1-propanol, and t-amyl alcohol. The hydroxyl moiety of 2-(3-hydroxypropyl) aminopyridine-N-oxide may be converted to a suitable leaving group, such as a halide, a mesylate, triflate, benzenesulfonate, etc., using conventional procedures. For example, 2-(3-hydroxypropyl)aminopyridine-N-oxide may be converted to the corresponding bromide by treatment with thionyl bromide or by treatment with hydrobromic acid and acetic acid. 2-(3-Bromopropyl) aminopyridine-N-oxide (as the hydrobromide salt) and [(S)-8-hydroxy-3-oxo-2-(2,2,2-trifluoro-ethyl)-2,3,4,5-tetrahydro-1H-benzo[c]azepin-4-yl]-acetic acid methyl ester may be coupled using a base, for example sodium hydroxide. Reduction of the pyridyl N-oxide may be accomplished under conventional conditions, more specifically, by treatment with zinc dust in methanol. Hydrolysis of the methyl or ethyl ester moiety (e.g., the —$CO_2R^3$ ester group of the compound of Formula (II) or (II-S)) was accomplished by treatment with aqueous base (NaOH). The product may be recrystallized from methanol/methyl t-butyl ether and hexane.

Abbreviations and symbols commonly used in the chemical arts are used herein to describe the compounds, reactions and reagents of this invention.

Certain radical groups may be abbreviated herein. The following definitions apply to the abbreviated radical groups: t-Bu refers to the tertiary butyl radical, Boc refers to the t-butyloxycarbonyl radical, Ph refers to the phenyl radical, CBZ refers to the benzyloxycarbonyl radical, Bn refers to the benzyl radical, Me refers to methyl, Et refers to ethyl, and Ac refers to acetyl.

The simple starting materials for preparing the compounds of this invention are commercially available or prepared by routine methods well known in the art.

The intermediate compounds of this invention are useful as intermediates in the preparation of pharmaceutically active compounds, in particular compounds which have fibrinogen and vitronectin antagonist properties.

EXAMPLES

Nuclear magnetic resonance spectra were recorded at 270 MHz. $CDCl_3$ is deuteriochloroform, DMSO-$d_6$ is hexadeuteriodimethylsulfoxide, and $CD_3OD$ is tetradeuteriomethanol. Chemical shifts are reported in parts per million (δ) downfield from the internal standard tetramethylsilane. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. HRMS indicates high resolution mass spectroscopy. Other abbreviations used herein include: EtOAc refers to ethyl acetate, MeOH refers to methanol, TFA refers to trifluoroacetic acid, THF refers to tetrahydrofuran, TBME refers to tert-butyl-methyl ether, $Et_3N$ or TEA refers to triethylamine, DCA refers to dicyclohexylamine, LDA refers to lithium diisopropyl amine, DCC refers to dicyclohexylcarbodiimide, DMAP refers to dimethylaminopyridine, DIEA refers to diisopropylethylamine, DMF refers to dimethyl formamide, and Pd—C refers to a palladium on carbon catalyst.

Example 1

6-Bromo-3-hydroxybenzaldehyde

3-Hydroxybenzaldehyde (120 g, 0.98 moles) was suspended in 2400 mL of $CH_2Cl_2$ in a 5 L 4-neck round bottom flask equipped with overhead stirrer, temperature probe, addition funnel, and condenser. The mixture was heated to 35-40° C. in order to dissolve the starting material. Bromine (52 mL, 1.0 moles, 1.02 eq.) was added dropwise through the addition funnel at a rate which maintained the reaction temperature between 35-38° C. The mixture was then allowed to stir overnight at 35° C. The mixture was slowly cooled to −5-0° C. over two hours and then allowed to stir at that temperature for 1 h more. The solid which formed was then collected by filtration through a Buchner funnel and the filter cake washed with 400 mL of a cold 1:1 $CH_2Cl_2$:heptane solution. The gray solid was then dried in vacuo (0.2 mm Hg) at room temperature. Yield=124.3 g (63%).

Example 2

2-[(2-Formyl-4-hydroxyphenyl)methylidene]succinic acid

6-Bromo-3-hydroxybenzaldehyde, 50 g, (from Example 1) was dissolved, with stirring, in 200 mL MeOH in a 500 mL Erlenmeyer flask. The resulting solution was filtered using a Buchner funnel lined with a glass microfibre filter. The filtered solution was charged into a 2 L 3-necked round bottomed flask, equipped with an air-driven mechanical stirrer, thermometer and reflux condenser, and stirred at room temperature for 2 hours. After confirmation by $^1$H-NMR that the dimethyl acetal is completely formed, Et$_3$N (111 ml) was added to the reaction flask followed by 500 mL CH$_3$CN. The reaction mixture was purged with N$_2$ followed by addition of 32.5 g itaconic acid, 0.56 g Pd (OAc)$_2$, 2.3 g P(o-tolyl)$_3$ and 8.0 g Bu$_4$NBr. The resulting reaction mixture was heated to reflux for 10 hours. After cooling to room temperature, about 550 mL of the reaction solvent was removed by rotary evaporation. Aqueous KOH solution (30 g in 200 mL water) was added, with stirring, at room temperature. The aqueous solution was washed with 200 mL TBME and the aqueous solution was acidified to pH 1 using 200 mL 3N HCl solution. The acidic aqueous solution was extracted with 200 mL TBME (4×). The combined TBME extracts were filtered through a glass microfiber lined Buchner funnel. The resulting solution was concentrated to minimum volume by rotary evaporation. Acetonitrile (200 mL) was added and the resulting mixture was concentrated by rotary evaporation (repeated 3 or 4 times). The final volume should be approx 250 mL. The heterogeneous solution was cooled to −10° C. for 2 hours and the resulting precipitate was filtered using a Buchner funnel and rinsed with a small amount of cold CH$_3$CN. The cream-colored solid product was dried under vacuum at 50° C. Yield=49.3(79%).

Example 3

(S)-2-Carboxyl-4-[(2-formyldimethylacetal-4-hydroxyphenyl)]butyric acid, bis(dicyclohexylamine) salt 2-[(2-Formyl-4-hydroxyphenyl)methylidene]succinic acid (Example 2) (50 g, 0.20 moles) was dissolved by heating in refluxing MeOH(450 mL) in a one liter three neck flask equipped with a condenser and an internal thermocouple. After 4 h at reflux, the solution was cooled to ambient temperature and filtered through Whatman #1 filter paper. The filtrate was placed in a 2 L Paar bottle and DCA(84 mL, 0.42 moles, 2.1 eq.) was added, followed by water(50 mL), and [RuCl$_2$(R-BINAP)]$_2$-TEA(250 mg, 0.5 wt %). The bottle was then placed in a Paar shaker and filled with 60 psi H$_2$, then evacuated. This fill and evacuate sequence was repeated twice more. The bottle was then filled with H$_2$ to 60 psi a fourth time and shaking commenced. The contents of the bottle were heated to 60° C. and the reaction monitored by $^1$H NMR. After 36 h the reaction was complete as determined by the presence of <2% (2-[(2-formyl-4-hydroxyphenyl)methylidene]succinic acid). The contents were allowed to cool to ambient temperature and were filtered through Whatman #1 filter paper. The filtrate was then concentrated by rotary evaporation to a volume of ~200 mL. CH$_3$CN(500 mL) was added and the mixture concentrated by rotary evaporation to ~200 mL. This acetonitrile addition and strip was conducted a total of three times at which point the mixture was allowed to stir at ambient temperature for 6 h. The solid was then collected on a Buchner funnel, rinsed with cold CH$_3$CN (100 mL) and dried in vacuo (40° C. @ 20 inches Hg). Yield=112 g (84%).

Example 4

Dimethyl (2S)-2-[(2-formyl-4-hydroxyphenyl)methyl]butanedioate (S)-2-Carboxyl-4-[(2-formyldimethylacetal-4-hydroxyphenyl)]butyric acid, bis(dicyclohexylamine) salt (300 g, 0.453 moles) was dissolved in 1200 mL of MeOH in a 3000 mL three neck flask equipped with a condenser, addition funnel, and temperature probe. Concentrated H$_2$SO$_4$(55.5 mL, 1.0 moles, 2.2 equiv.) was slowly added dropwise to the stirred solution. After addition was complete, the mixture was heated to reflux and the reaction monitored by HPLC. After 19 h, the reaction was complete as observed by HPLC. The mixture was allowed to cool to r.t. and the solvent was removed by rotary evaporation. EtOAc(1000 mL) was added and the solvent removed by rotary evaporation (repeated 1×) (1000 mL removed). The precipitated DCA salts, which had formed were then removed by filtration of the mixture through Whatman #1 paper. The filter cake was rinsed with EtOAc (200 mL). The wet cake weighed 135 grams. The filtrate was washed with H$_2$O (2×500 mL), 10 vol % H$_2$SO$_4$(1×500 mL) and saturated aqueous NaHCO$_3$ (1×500 mL). The organic layer was concentrated by rotary evaporation. CH$_3$CN (500 mL) was added and the mixture concentrated (repeated 1×). A final portion of CH$_3$CN (400 mL) was added. The solution was then assayed for (S)-2-(2-Formyl-4-hydroxy-benzyl)-succinic acid dimethyl ester used as is. Total wt. of solution=696.2 g. Assay=15.8 wt %. Yield=110 g(86%).

Example 5

[(S)-8-Hydroxy-3-oxo-2-(2,2,2-trifluoro-ethyl)-2,3,4,5-tetrahydro-1H-benzo[c]azepin-4-yl]-acetic acid methyl ester A mixture of (S)-2-(2-formyl-4-hydroxy-benzyl)-succinic acid dimethyl ester in CH$_3$CN (259 g of solution, 15.4% w/w assay, 40.0 g (S)-2-(2-formylhydroxy-benzyl)-succinic acid dimethyl ester, 0.14 mol), trifluoroethylamine-HCl (23.0 g, 1.2 eq, 0.17 mol) and ZnCl$_2$ (9.5 g, 0.5 eq, 0.07 mol) was heated to reflux for 2 hours in a 1 L round bottom flask, equipped with a Dean-Stark trap and condenser. A total of 80 ml of solvent was collected in the Dean-Stark trap.

After cooling to room temperature, a solution of 65.7 g NaBH(OAc)$_3$ (2.2 eq, 0.31 mol) in 200 mL DMF was slowly added, with stirring. Stirring was continued for 15 minutes at RT. The pH of the solution was adjusted to 6-6.5 by adding 400 mL saturated NaHCO$_3$ solution. The resulting solution was extracted with 200 mL EtOAc (2×), the combined EtOAc extracts were filtered and concentrated. Toluene (200 ml) was added and the resulting mixture was concentrated by rotary evaporation. Repeat. The resulting residue was dissolved in 300 mL toluene and 8 mL TFA, and resulting solution was heated to reflux for 24 hours, then cooled to RT. The reaction solution was concentrated by rotary evaporation, then diluted with 200 mL EtOAc, washed with 200 mL saturated NaHCO$_3$ (2×), then concentrated to minimum volume by rotary evaporation. Toluene (200 mL) was added to the residue, then 200 mL was removed from solution by rotary evaporation. Tolune (100 mL) was added, followed by removal of 50 mL solvent by rotary evaporation. The resulting mixture was cooled to 0° C. for 0.5 hour and the solid material was filtered through a Buchner funnel and dried. The product may be dried to constant weight in a vacuum oven at 60° C. Yield=34.0 g(72%).

Example 6

2-(2-{[tert-Butoxycarbonyl-(2,2,2-trifluoro-ethyl)-amino]-methyl}-4-methoxy-benzylidene)-succinic acid A 1-L, 3 neck flask fitted with a thermocouple and reflux condenser was charged with acetonitrile (240 mL, 6 volumes) and mechanical stirring began. The following reagents were then charged to the flask: (2-Bromo-5-methoxy-benzyl)-(2,2,2-trifluoro-ethyl)-carbamic acid butyl ester (40.0 g, 0.100 mol, 1.0 eq.), potassium carbonate (17.97 g, 0.130 mol, 1.3 eq.), itaconic acid (15.61 g, 0.120 mol, 1.2 eq) to give a white slurry. At this time, water (80 mL, 2 volumes) was added and the temperature cooled upon addition as carbon dioxide was evolved. After $CO_2$ evolution ceased, the solution was degassed by placing the vessel under vacuum for one minute and then filling with nitrogen for two minutes. This procedure was repeated 3 times leaving the solution under a nitrogen atmosphere. Palladium acetate (1.12 g, 5.0 mmol, 0.05 eq.) and tri-o-tolyl phosphine (3.04 g, 10.0 mmol, 0.10 eq.) were added in a single portion. The degassing procedure was repeated an additional three times, leaving the vessel under nitrogen atmosphere. The solution was heated to reflux over 25 minutes at which time the internal temperature reached 78° C. After 19.5 h (overnight), HPLC analysis indicated that the reaction was complete. The reaction was allowed to cool to room temperature over thirty minutes. The solution was transferred to a 1 L flask and 220 mL of acetonitrile were removed by rotary evaporation. The aqueous layer was transferred back to a 1 L 3-necked flask rinsing with ethyl acetate (320 ml, 8 volumes) with a 60 mL addition funnel, thermocouple, pH probe (pH=6.93) and mechanical stirrer and cooled in an ice bath over 30 min. The addition funnel was charged with 20 mL of concentrated HCl, which was added dropwise to the solution while stirring. The internal temperature was kept below 11° C. by controlling the rate of addition by hand. After adding 16 ml (0.192 mol, 1.92 eq) of concentrated HCl the pH had reached 2.83. The solution was poured into a 1-L separatory funnel and was agitated. The layers were separated and the aqueous layer was washed two additional times, at which time the aqueous layer showed no sign of product, by HPLC. The combined organic phases were filtered through Whatman quality 1 filter paper to remove trace solids and provide a clear solution. The filtrate was then stripped to 20% of the original volume by removing 760 mL of EtOAc on the rotary evaporator. Acetonitrile (400 mL, 10 volumes) was added and the solution was stirred rapidly, then heated to reflux over 30 minutes. Heating was continued until solution was clear. At this point, the solution was allowed to cool to room temperature. The resulting slurry was cooled to 0-5° C. over 30 minutes and held at that temperature for 1.5 hours. The off-white precipitate was collected on a Buchner funnel, and was dried, with heating (70° C.) in a vacuum oven for 48 h to give a white powder 38.93 g (87 mmol, 87.0% yield).

Example 7

(S)-2-(2-{[tert-Butoxycarbonyl-(2,2,2-trifluoro-ethyl)-amino]-methyl}-4-methoxy-benzyl)-succinic acid bis-dicyclohexylamine salt 2-(2-{[tert-Butoxycarbonyl-(2,2,2-trifluoro-ethyl)-amino]-methyl}-4-methoxy-benzylidene)-succinic acid (100.0 g, 0.224 mol), [RuCl$_2$(R-BINAP)]$_2$-TEA (300 mg, 0.3 wt. %), MeOH (900 mL), dicyclohexylamine (89.2 g, 0.49 mol), and $H_2O$ (100 mL) was charged into a 2 L Parr bottle, and attached to the Parr hydrogenation apparatus. The Parr bottle was purged six times with 30 psi H2. Hydrogenation was conducted, with shaking at 30-35 psi $H_2$, at 60° C. for 20 h. The reaction mixture was cooled and concentrated in vacuo. Acetonitrile was added (2 L) and reconcentrated. Fresh acetonitrile (1 L) was added and the resulting mixture was stirred for 2 h. The resultant solid was collected by filtration and washed with $CH_3CN$ (100 mL). If desired, recrystallization from $CH_3CN$ (1 L) may be performed. The material was partitioned between 10% aq $H_2SO_4$ (700 mL) and EtOAc (1400 mL). The aqueous phase was washed with EtOAc (300 mL). The combined EtOAc phases were washed with $H_2O$ (3×650 mL), 20% NaCl soln (650 mL), then dried over $MgSO_4$ (30 g), and concentrated in vacuo to give (S)-2-(2-{[tert-butoxycarbonyl-(2,2,2-trifluoro-ethyl)-amino]-methyl}-4-methoxy-benzyl)-succinic acid bis dicyclohexyl amine salt as a glass (78.9 g).

Example 8

(S)-2-{4-Methoxy-2-[(2,2,2-trifluoro-ethylamino)-methyl]-benzyl}-succinic acid dimethyl ester (S)-2-(2-{[tert-Butoxycarbonyl-(2,2,2-trifluoro-ethyl)-amino]-methyl}methoxy-benzyl)-succinic acid bis-dicyclohexylamine salt was dissolved in a mixture of dichloromethane and 5.66% aq $H_2SO_4$. The layers were separated and the aqueous layer further extracted with dichloromethane. The combined dichloromethane layers were washed with water to pH ~4.5. After removal of the most dichloromethane by distillation under atmospheric pressure, methanol was added, then concentrated by vacuum distillation. Fresh methanol was added, and upon cooling to ~10° C., HCl (gas) was added while maintaining temperature below 20° C. When the reaction was complete, the mixture was cooled to ~10° C. and neutralized with saturated $NaHCO_3$ to bring the pH to about 7, followed by vacuum distillation to remove the most of methanol. The mixture was extracted with toluene. The layers were separated and the toluene layer was washed with water.

Example 9

[(S)-8-Methoxy-3-oxo-2-(2,2,2-trifluoro-ethyl)-2,3,4,5-tetrahydro-1H-benzo[c]azepin-4-yl]-acetic acid methyl ester A toluene solution S)-2-{4-methoxy-2-[(2,2,2-trifluoro-ethylamino)-methyl]-benzyl}-succinic acid dimethyl ester (950 mL, 212 mmol) was placed in a 2 L round bottom flask and concentrated under rotary evaporation to a volume of 460 mL (to remove residual water). Toluene (450 mL) was added and the mixture was transferred to a 3 neck 2 L flask. The flask was fitted with reflux condenser, thermometer, nitrogen inlet/outlet, and stir bar. The mixture was de-gassed under a flow of nitrogen gas. The mixture was heated to 50° C. and trifluoroacetic acid (200 mmol, 22.8 g) was added over a 5 min period. The mixture was heated to reflux. After 2.5 h, HPLC analysis (Waters Cosmosil 4.6×150 mm, 60% $CH_3CN$/40% 0.1% TFA, 220 nm, 0.5 mL/min) showed less than 0.2% (area %) of (S)-2-{4-methoxy-2-[(2,2,2-trifluoro-ethylamino)-methyl]-benzyl}-succinic acid dimethyl ester remaining. The mixture was cooled to 25° C. and was washed with 1×400 ml $NaHCO_3$ solution (satd.), and 1×400 mL water. The solvent was removed by vacuum distillation.

The residue was treated with hexane (800 ml) and was heated to reflux with rapid stirring. This resulted in a solution with some oily residue. Toluene (20 mL) was added and a clear solution was obtained. The mixture was allowed to cool to 25° C. with rapid stirring over a 1 hour period. The mixture was then cooled to 0-5° C. for 1 hour. The resulting solid was isolated by filtration, washed with hexane (70 mL) and air dried to provide the product as an off-white solid (64.4 g, 88%).

Example 10

[(S)-8-Hydroxy-3-oxo-2-(2,2,2-trifluoro-ethyl)-2,3, 4,5-tetrahydro-1H-benzo[c]azepin-4-yl]-acetic acid methyl ester A 5 L, 3-necked, round-bottom flask equipped with an air-driven mechanical stirrer, was charged with methylene chloride (1530 g, 1160 mL) then cooled to −5° C. in a dry ice-isopropanol bath. Boron tribromide (680.7 g, 257 mL, 2.72 mol, 3.8 eq) was added at such a rate that the temperature was maintained <2° C. The reaction was cooled to −8° C. and a solution of the non-racemic methyl ether, [(S)-8-methoxy-3-oxo-2-(2,2,2-trifluoro-ethyl)-2,3,4,5-tetrahydro-1H-benzo[c]azepin-4-yl]-acetic acid methyl ester (246.9 g, 0.715 mol, 1 eq) in methylene chloride (1530 g, 1160 mL) was added dropwise at a temperature of −8 to −2° C. The reaction was continued at −2° C. The reaction was deemed complete when the HPLC of the reaction had <0.3% of [(S)-8-methoxy-3-oxo-2-(2,2,2-trifluoro-ethyl)-2,3,4,5-tetrahydro-1H-benzo[c]azepin-4-yl]-acetic acid methyl ester. The reaction was then slowly transferred into methanol (1030 g, 1303 mL, 45 eq (5.3 vol)), stirred in a 12-L 3 neck flask at −35° C., cooled with dry ice-isopropanol.

The resulting mixture was maintained at <−20° C., and treated dropwise with saturated sodium carbonate to pH 6-7 (required approximately 2.0 L(8.1 vol)). The resulting solution was transferred to a 12-L separatory funnel with a chloroform rinse (1.23 L) and the layers separated. After extraction of the aqueous layer with chloroform, the combined organic layers were washed with 3% sodium chloride followed by brine. The organic layer (3.7 L) was distilled at reduced pressure to ½ volume at <35° C. and hexane (740 mL) was added at which time a precipitate was present. About 600 mL of solvent was distilled. The solution was cooled to 5° C. and stirred for 1 hr. The product was collected and further washed with some of the cold filtrate (ca. 300 mL), and hexane (80 g, 124 mL). After air drying, the product was dried at 38-40° C. at 12 mm of Hg for 15 h, to produce [(S)-8-hydroxy-3-oxo-2-(2,2,2-trifluoro-ethyl)-2,3,4,5-tetrahydro-1H-benzo[c]azepin-4-yl]-acetic acid methyl ester in 91.0% yield; 214.1 g (theory 236.8 g).

Example 11

2-(tert)-Butoxycarbonylamino-6-picoline

To a 10 gallon glass-lined reactor vessel was added toluene (10.4 L), di-tert-butyldicarbonate (16.3 kg, 74.68 mol), and 6-methyl-pyridin-2-ylamine (6.75 kg, 62.465 mol). The reaction vessel was purged with nitrogen then was heated to 106.5° C. for 14 hours. The reactor was cooled to 31° C. and the toluene was removed under vacuum. The final reactor temperature was 40.1° C. Heptane (6.7 L) was added. The resulting mixture was stirred for 15 minutes then filtered through celite 545 (0.67 kg) using a Sparkler filter. The reaction mixture was kept warm (35-40° C.) by applying steam to the Sparkler filter. The filter cake was washed with 1.5 L of heptane and the filtrate was placed back in the reactor vessel. The contents of the reactor were cooled to −21.7° C. over 1 hour and held at that temperature for 20 hours. The solids that formed were collected by filtration using a centrifuge. The resulting solid was washed with cold heptane (1.5 L) and dried under vacuum for 24.5 hours to give 8.65 kg of the title product (41.59 mol, 66.6% crude yield).

Example 12

1,1-Dimethylethyl methyl(6-methyl-2-pyridinyl)carbamate

A 1 L round bottom flask was charged with THF (200 mL) and sodium hydride (60% in mineral oil, 22 g, 0.55 mol). A solution of 2-(tert)-butoxycarbonylamino)-6-picoline (100 g, 99.2% PAR, 0.48 mol) in THF (200 mL) was added over 45 minutes while maintaining temperature 20-25° C. The resulting mixture was stirred for 15 minutes followed by addition of iodomethane (102 mL, 1.64 mol) over 1 h, while maintaining temperature 20-25° C. The resulting mixture was stirred for 3 h at room temperature. Deionized $H_2O$ (100 ml) was added and the two layers separated. The aqueous layer was extracted with hexane (150 mL). The combined organic layers were washed with deionized $H_2O$ (2×100 mL) and concentrated to provide the title product (107.6 g).

Example 13

Ethyl 6-[[(1,1-dimethylethoxy)carbonyl]methylamino]-2-pyridineacetate

A 2 L 3-necked flask equipped with air driven mechanical stirrer, thermometer, addition funnel and nitrogen inlet/outlet was charged with THF (80 mL), 1,1-dimethylethyl methyl(6-methyl-2-pyridinyl)carbamate (80 g, 0.36 mol) and diethyl carbonate (157.2 mL, 1.30 mol). The flask was cooled until the internal temperature is −15° C. LDA (450 mL, 0.9 mol) was added over 1 h while maintaining temperature <−10° C. The reaction mixture was transferred to another flask which contain saturated $NH_4Cl$ (400 mL). The two layers were separated; the aqueous layer was extracted with ethyl acetate (2×150 mL). The organic layers were washed with deionized $H_2O$ (4×150 mL), combined, and concentrated to provide the tide compound. Evaporate the solvent and weigh the product (124.7 g).

Example 14

6-(Methylamino)-2-pyridineethanol

A clean dry 2 L 3 necked flask was fitted with reflux condenser, addition funnel, stir bar, nitrogen inlet and outlet, temperature sensor, and heating mantle. The flask was purged using a stream of nitrogen. Lithium borohydride (4.36 g, 200 mmol) was added all at once. Tetrahydrofuran (THF, 150 mL) was charged into the addition funnel and was added to the solid with stirring over a 10-minute period. After dissolution, the mixture was heated to 66° C. Ethyl 6-[[(1,1-dimethylethoxy)carbonyl]methylamino]-2-pyridineacetate (110 g, 374 mmol) was dissolved in THF (400 ml) and charged into the addition funnel. The ethyl 6-[[(1,1-dimethylethoxy)carbonyl]methylamino]-2-pyridineacetate solution was added to the $LiBH_4$ solution in as dropwise manner over a period of 25 minutes. The addition rate was controlled so as to maintain a gentle reflux. The mixture was heated to reflux for 5 h, the heat was turned off, and the reaction was allowed to stir overnight at 23° C. The reaction mixture was cooled to 10° C. and was treated with water (250 mL) in a dropwise manner. The mixture was stirred for 30 min and ethyl acetate (250 mL) was added. The mixture was stirred for 5 minutes and the layers were allowed to separate. The organic layer was washed with 2×250 mL saturated sodium chloride. The organic layers were stripped to thick oil in a 2 L round bottom flask. The residue was dissolved in ethyl acetate (200 mL) and was extracted with 1 N HCl (2×250 mL). The organic layer was discarded and the acid layer was placed in a 2 L 3 neck round bottom flask. The flask was heated to 50° C. for 1 h. The mixture was cooled to 10° C. and the solution was treated with 4 N NaOH (~350 mL) to a pH of 10. The basic solution was extracted with ethyl acetate (3×150 mL). Care was taken to keep the pH of the aqueous phase above pH=9. The ethyl acetate extracts were combined, washed with water (150 mL) and concentrated to provide the title compound as a thin yellow oil, 33.5 g, yield=58%)

Example 15

S-(−)-8-[2-[6-(Methylamino)pyridin-2-yl]-1-ethoxy]-3-oxo-2-(2,2,2-trifluoroethyl)-1,2,4,5-tetrahydro-2-benzazepine-4-acetic acid A 2.0 L 3-necked round bottomed flask, under nitrogen, was fitted with an air-driven mechanical stirrer, thermometer, and dropping funnel. To, the empty flask was charged [(S)-8-hydroxy-3-oxo-2-(2,2,2-trifluoro-ethyl-2,3,4,5-tetrahydro-1H-benzo[c]azepin-4-yl]-acetic acid methyl ester (45.5 g, 0.14 mol., 1.0 equivalent) and TBME (500 mL). To the heterogeneous [(S)-8-hydroxy-3-oxo-2-(2,2,2-trifluoro-ethyl)-2,3,4,5-tetrahydro-1H-benzo[c]azepin-4-yl]-acetic acid methyl ester/TBME mixture was added in one portion, a TBME solution (250 mL TBME) of 6-(methylamino)-2-pyridineethanol (25.0 g, 0.15 mol., 1.1 equivalents). To the mixture was added triphenylphosphine (39.7 g, 0.15 mol., 1.1 equivalents). The heterogeneous mixture was cooled to 3° C.-5° C. To the cooled mixture was dropwise added over 13-15 minutes, a solution of diisopropylazodicarboxylate (DIAD, 30.6 g, 0.15 mol., 1.1 equivalents) in TBME (60 ml). The ice-bath was removed and the reaction mixture was stirred at room temperature (18° C.-20° C.). Alternatively, the triphenylphosphine-containing reaction mixture, in toluene or TBME, may be maintained at about room temperature and the DIAD, in toluene or TBME, may be added at room temperature over a period of about 1.5 hours. In another embodiment, the triphenylphosphine-containing reaction mixture, in toluene or TBME, may be maintained at a temperature of about 22° C. and the DIAD, in toluene or TBME, may be added at a temperature of about 22° C. over a period of about 1.5 hours.

After 3 hours, the mixture was concentrated by rotary evaporation to one-third of its original volume(~500 mL TBME removed). The mixture was cooled to 0° C.-2° C. for 30 minutes. The mixture was filtered through qualitative filter paper. The filtrate was extracted with 3 N NaOH(100 mL). The layers were separated and the organic layer was extracted with brine(100 mL). To the mixture was added in one portion, an aqueous solution (125 mL H$_2$O) of lithium hydroxide monohydrate (11.4 g, 0.27 mol., 2.2 equivalents). The mixture was heated at 50° C.-55° C. After about 30 minutes to 1 hour, the mixture was cooled to room temperature, and diluted with H$_2$O (375 mL). The layers were separated and the aqueous layer was extracted with fresh TBME (250 mL). The layers were separated. To the aqueous layer was added methanol (125 mL). The aqueous methanolic mixture was acidified with concentrated HCl (10-12 mL) until pH=6.7. The mixture was seeded with authentic S-(−)-8-[2-[6-(methylamino)pyridin-2-yl]-1-ethoxy]-3-oxo-2-(2,2,2-trifluoroethyl)-1,2,4,5-tetrahydro-2-benzazepine-4-acetic acid. The mixture was further acidified with concentrated HCl (10-12 mL) until pH=5.2 (S-(−)-8-[2-[6-(methylamino)pyridin-2-yl]-1-ethoxy]-3-oxo-2-(2,2,2-trifluoroethyl)-1,2,4,5-tetrahydro-2-benzazepine-4-acetic acid starts to precipitate at pH=6.4). The mixture was cooled to 0° C.-2° C. for 30 minutes. The precipitated S-(−)-8-[2-[6-(methylamino)pyridin-2-yl]-1-ethoxy]-3-oxo-2-(2,2,2-trifluoroethyl)-1,2,4,5-tetrahydro-2-benzazepine-4-acetic acid was collected by filtration and dried for 15 minutes. The crude S-(−)-8-[2-[6-(methylamino)pyridin-2-yl]-1-ethoxy]-3-oxo-2-(2,2,2-trifluoroethyl)-1,2,4,5-tetrahydro-2-benzazepine-4-acetic acid precipitate was dissolved in hot methanol (450 mL), filtered through qualitative filter paper, seeded with authentic material, and allowed to stand at room temperature for 16 hours. The recrystallized title compound was collected by filtration and dried for 15 minutes. The recrsytallized title compound, [(S)-8-[2-(6-methylamino-pyridin-2-yl)-ethoxy]-3-oxo-2-(2,2,2-trifluoro-ethyl)-2,3,4,5-tetrahydro-1-H-benzo[c]azepin-4-yl]-acetic acid, was taken up in water (165 mL) and heated at 65° C.-70° C. for 30 minutes. The mixture was cooled to room temperature and the slurried material was collected by filtration. The title compound was oven dried in-vacuo (65° C.-70° C., 1.0 mm Hg) to constant weight(2-4 hours). The dried title compound was isolated in 56% yield, and assayed (HPLC) at 98.3%.

Example 16

2-(3-Hydroxypropyl)aminopyridine-N-oxide

A mixture of 2-chloro-pyridine-N-oxide (one molar equivalent), 3-amino-1-propanol (about 2 molar equivalents), and sodium bicarbonate (about 2 molar equivalents) was heated to about 90° C. in t-amyl alcohol until HPLC analysis indicates <3% area 2-chloro-pyridine-N-oxide. Additional 3-amino-1-propanol may be added to complete the reaction. The mixture is cooled to about 25-32° C. and is treated with a 4:1(v/v) mixture of ethyl acetate:methanol. The mixture was filtered and the filter cake was rinsed with additional 4:1(v/v) ethyl acetate:methanol. The combined filtrates were concentrated by distillation, and methanol and ethyl acetate were added. The mixture was cooled to about 50-60° C. and filtered. Methanol was added to the filtrate, followed by hexane. The mixture was allowed to cool and seed crystals of 3-(1-oxy-pyridin-2-ylamino)-propan-1-ol were added during the cooling process. The product was isolated by filtration, rinsing the filter cake with cold hexane and drying.

Representative HPLC conditions: Column: YMC ODS-aq, C18 S, 5 μ; 4.6×250 mm; Mobile phase: 10:90 acetonitrile:water with 0.1% trifluoroacetic acid, Flow rate: 0.9 mL/m; Detection: UV, 255 nm, Injection volume: 20 μL, Temperature: ambient Example 17

N-(3-Bromopropyl)-2-pyridinamine-1-oxide hydrogenbromide

A solution 3-(1-Oxy-pyridin-2-ylamino)-propan-1-ol (one molar equivalent) in methylene chloride was treated with thionyl bromide (about 1.2 molar equivalents) while maintaining the temperature below about 25° C. The resulting solution was stirred until HPLC analysis indicates <2% area 3-(1-oxy-pyridin-2-ylamino)-propan-1-ol. The mixture was filtered and the filter cake was rinsed with methylene chloride. The filtrates were concentrated by atmospheric distillation and methyl t-butyl ether was added to the warm solution. Additional solvent was distilled and the mixture was allowed to cool to about 20-25° C. Methyl t-butyl ether was added and the mixture was cooled to about 0-5° C. The mixture was filtered and the filter cake was rinsed with methyl t-butyl ether and dried.

Representative HPLC conditions: Column: Zorbax SB-C18; 4.6 mm×7.5 cm, Mobile Phase: 30:70 acetonitrile: water, Flow rate: 1 mL/min, Detection: UV, 240 nm, Injection volume: 5 μL, Temperature: ambient All solvents and reagents are accepted on vendor specifications, and may be checked for identity by spectroscopic or chromatographic comparison with authentic samples. Unless indicated otherwise, raw materials are typically ≧95% pure as purchased from the supplier.

The above description fully discloses how to make and use the present invention. However, the present invention is not limited to the particular embodiments described hereinabove, but includes all modifications thereof within the scope of the following claims. The various references to journals, patents and other publications which are cited herein comprises the state of the art and are incorporated herein by reference as though fully set forth.

We claim:
1. A process for preparing a compound of Formula (I):

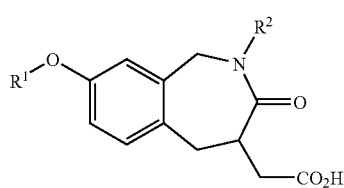

(I)

from a benzazepine-phenol of Formula (II):

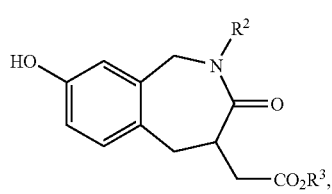

(II)

wherein the benzazepine-phenol of Formula (II) is prepared by a process comprising converting a compound of Formula (III):

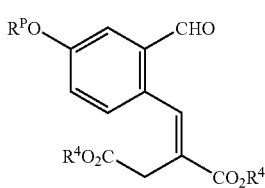

(III)

to a compound of Formula (IV):

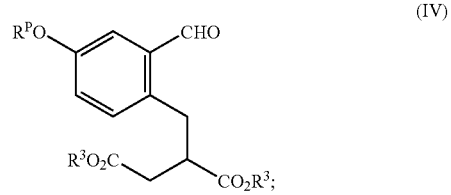

(IV)

wherein:
$R^P$ is H or a suitable phenol protecting group;
$R^3$ and $R^4$ are the same or different and are each independently H or a carboxylic acid ester protecting group;
$R^2$ is $R^7$, $C_1$-$C_4$ alkyl, $C_1$-$C_4$ haloalkyl, A-$C_0$-$C_4$ alkyl-, A-$C_2$-$C_4$ alkenyl-, A-$C_2$-$C_4$ alkynyl-, A-$C_3$-$C_4$ oxoalkenyl-, A-$C_3$-$C_4$ oxoalkynyl-, A-$C_0$-$C_4$ aminoalkyl-, A-$C_3$-$C_4$ aminoalkenyl-, A-$C_3$-$C_4$ aminoalkynyl-, optionally substituted by any accessible combination of one or more $R^{10}$ $R^7$;
A is H, $C_3$-$C_6$ cycloalkyl, Het or Ar;
$R^7$ is —$COR^8$, $COCR'_2R^9$, —$C(S)R^8$, —$S(O)_mOR'$, —$S(O)_mNR'R''$, —$PO(OR')$, —$PO(OR')_2$, —$NO_2$, or tetrazolyl;
each $R^8$ independently is —OR', —NR'R'', —NR'$SO_2$R', —NR'OR', or —$OCR'_2CO(O)R'$;
$R^9$ is —OR', —CN, —S(O)$_r$R', —S(O)$_m$NR'$_2$, —C(O)R', C(O)NR'$_2$, or —$CO_2$R';
$R^{10}$ is H, halo, —$OR^{11}$, —CN, —NR'$R^{11}$, —$NO_2$, —$CF_3$, $CF_3S(O)_r$—, —$CO_2R'$, —$CONR'_2$, A-$C_0$-$C_6$ alkyl-, A-$C_1$-$C_6$ oxoalkyl-, A-$C_2$-$C_6$ alkenyl-, A-$C_2$-$C_6$ alkynyl-, A-$C_0$-$C_6$ alkyloxy-, A-$C_0$-$C_6$ alkylamino—or A-$C_0$-$C_6$ alkyl-S(O)$_r$-;
$R^{11}$ is R', C(O)R', —C(O)NR'$_2$, —C(O)OR', —S(O)$_m$R', or —S(O)$_m$NR'$_2$;
$R^1$ is

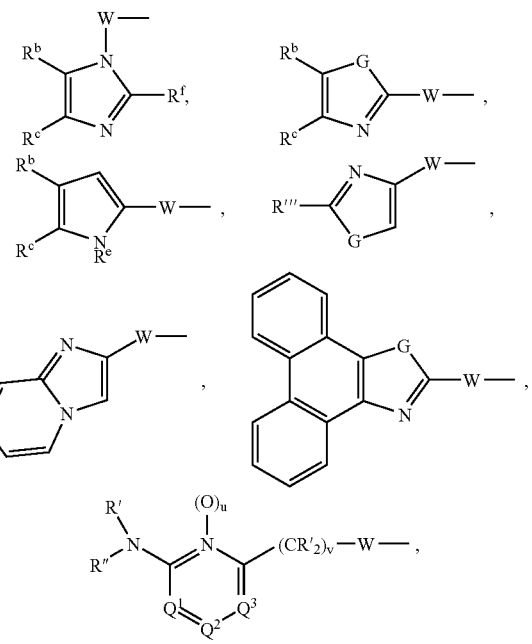

-continued

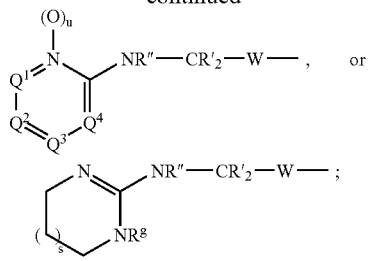

W is —(CHR$^g$)$_a$—U—(CHR$^g$)$_b$—;
U is absent or CO, CR$^g_2$, C(=CR$^g_2$), S(O)$_k$, O, NR$^g$, CR$^g$OR$^g$, CR$^g$(OR$^k$)CR$^g_2$, CR$^g_2$CR$^g$(OR$^k$), C(O)CR$_2$, CR$^g_2$C(O), CONR$^i$, NR$^i$CO, OC(O), C(O)O, C(S)O, OC(S), C(S)NR$^g$, NR$^g$C(S), S(O)$_2$NR$^g$, NR$^g$S(O)$_2$ N=N, NR$^g$NR$^g$, NR$^g$CR$^g_2$, CR$^g_2$NR$^5$, CR$^g_2$O OCR$^g_2$, C≡C or CR$^g$=CR$^g$;
G is NR$^e$, S or O;
R$^g$ is H, C$_1$-C$_6$ alkyl, Het-C$_0$-C$_6$ alkyl, C$_3$-C$_7$ cycloalkyl-C$_0$-C$_6$ alkyl or Ar—C$_0$-C$_6$ alkyl;
R$^k$ is R$^g$, —C(O)R$^g$, or —C(O)OR$^f$;
R$^i$ is H, C$_1$-C$_6$ alkyl, Het-C$_0$-C$_6$ alkyl, C$_3$-C$_7$ cycloalkyl-C$_0$-C$_6$ alkyl, Ar—C$_0$-C$_6$ alkyl, or C$_1$-C$_6$ alkyl substituted by one to three groups chosen from halogen, CN, NR$^g_2$, OR$^g$, SR$^g$, CO$_2$R$^g$, and CON(R$^g$)$_2$;
R$^f$ is H, C$_1$-C$_6$ alkyl or Ar—C$_0$-C$_6$ alkyl;
R$^e$ is H, C$_1$-C$_6$ alkyl, Ar—C$_0$-C$_6$ alkyl, Het-C$_0$-C$_6$ alkyl, C$_3$-C$_7$ cycloalkyl-C$_0$-C$_6$ alkyl, or (CH$_2$)$_k$CO$_2$R$^g$;
R$^b$ and R$^c$ are independently selected from H, C$_1$-C$_6$ alkyl, Ar—C$_0$-C$_6$ alkyl, Het-C$_0$-C$_6$ alkyl, or C$_3$-C$_6$ cycloalkyl-C$_0$-C$_6$ alkyl, halogen, CF$_3$, OR$^f$, S(O)$_k$R$^f$, COR$^f$, NO$_2$, N(R$^f$)$_2$, CO(NR$^f$)$_2$, CH$_2$N(R$^f$)$_2$, or R$^b$ and R$^c$ are joined together to form a five or six membered aromatic or non-aromatic carbocyclic or heterocyclic ring, optionally substituted by up to three substituents chosen from halogen, CF$_3$, C$_1$-C$_4$ alkyl, OR$^f$, S(O)$_k$R$^f$, COR$^f$, CO$_2$R$^f$, OH, NO$_2$, N(R$^f$)$_2$, CO(NR$^f$)$_2$, and CH$_2$N (R$^{(Rf)}$)$_2$; or methylenedioxy;
R$^b$ and R$^c$ are independently selected from H, C$_1$-C$_6$ alkyl, Ar—C$_0$-C$_6$ alkyl, Het-C$_0$-C$_6$ alkyl, or C$_3$-C$_6$ cycloalkyl-C$_0$-C$_6$ alkyl, halogen, CF$_3$, OR$^f$, S(O)$_k$R$^f$, COR$^f$, NO$_2$, N(R$^f$)$_2$, CO(NR$^f$)$_2$, CH$_2$N(R$^f$)$_2$, or R$^b$ and R$^c$ are joined together to form a five or six membered aromatic or non-aromatic carbocyclic or heterocyclic ring, optionally substituted by up to three substituents chosen from halogen, CF$_3$, C$_1$-C$_4$ alkyl, OR$^f$, S(O)$_k$R$^f$, COR$^f$, CO$_2$R$^f$, OH, NO$_2$, N(R$^f$)$_2$, CO(NR$^f$)$_2$, and CH$_2$N (R$^{(Rf)}$)$_2$; or methylenedioxy;
Q$^1$, Q$^2$, Q$^3$ and Q$^4$ are independently N or C—R$^y$, provided that no more than one of Q$^1$, Q$^2$, Q$^3$ and Q$^4$ is N;
R' is H, C$_1$-C$_6$ alkyl, Ar—C$_0$-C$_6$ alkyl or C$_3$-C$_6$ cycloalkyl-C$_0$-C$_6$ alkyl;
R" is R', —C(O)R' or —C(O)OR';
R'" is H, C$_1$-C$_6$ alkyl, Ar—C$_0$-C$_6$ alkyl, Het-C$_0$-C$_6$ alkyl, or C$_3$-C$_6$ cycloalkyl-C$_0$-C$_6$ alkyl, halogen, CF$_3$, OR$^f$, S(O)$_k$R$^f$, COR$^f$, NO$_2$, N(R$^f$)$_2$, CO(NR$^f$)$_2$, CH$_2$N(R$^f$)$_2$;
R$^y$ is H, halo, —OR$^g$, —SR$^g$, —CN, —NR$^g$R$^k$, —NO$_2$, —CF$_3$, CF$_3$S(O)$_r$—, —CO$_2$R$^g$, —COR$^g$ or —CONR$^g_2$, or C$_1$-C$_6$ alkyl optionally substituted by halo, —OR$^g$, —SR$^g$, —CN, —NR$^g$R", —NO$_2$, —CF$_3$, R'S(O)$_r$—, —CO$_2$R$^g$, —COR$^g$ or —CONR$^g_2$;
a is 0, 1 or 2;
b is 0, 1 or 2;
k is 0, 1 or 2;
m is 1 or 2;
r is 0, 1 or 2;
s is 0, 1 or 2;
u is 0 or 1; and
v is 0 or 1;
or a pharmaceutically acceptable salt thereof.

2. A process according to claim 1, comprising preparing a compound of Formula (I-S):

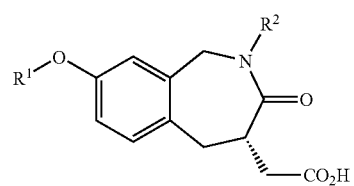

from a benzazepine-phenol of Formula (II-S):

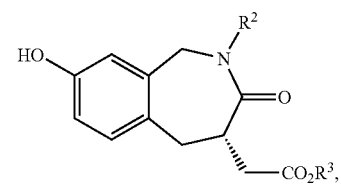

wherein the benzazepine-phenol of Formula (II-S) is prepared by a process comprising converting a compound of Formula (III):

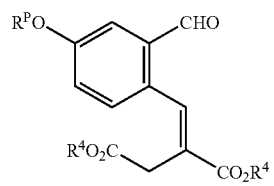

to a compound of Formula (IV-S):

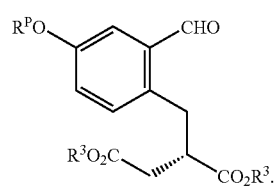

3. A process according to claim 1, further comprising a process for preparing the compound of Formula (II) comprising the steps of:

1) treating a compound having Formula (a)

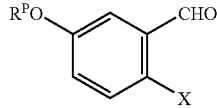

(a)

wherein $R^P$ is H or a suitable phenol protecting group and X is halogen, —$OSO_2F$, or —$OSO_2CF_3$, with a compound having the formula:

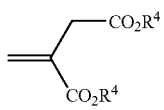

to form a compound of Formula (b)

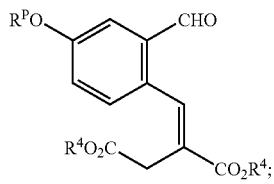

(b)

2) converting the compound of Formula (b) to a compound of Formula (c);

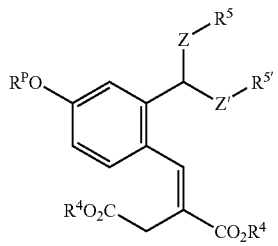

(c)

wherein $R^5$ and $R^{5'}$ are $C_1$-$C_4$ alkyl or $R^5$ and $R^{5'}$, taken together with the atoms to which they are attached form a saturated 5- or 6-membered heterocyclic ring and Z and Z' are independently selected from O, NH or $NCH_3$;

3) converting the compound of Formula (c) to a compound of Formula (d):

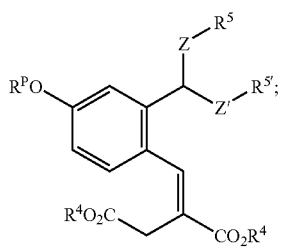

(d)

4) converting the compound of Formula (d) to a compound of Formula (e)

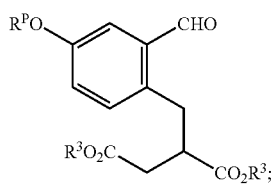

(e)

5) converting the compound of Formula (e) to a compound of Formula (f)

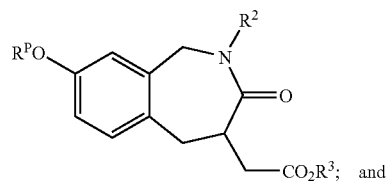

(f)

and 6) converting the compound of Formula (f) to a compound of Formula (II).

4. A process according to claim 1, further comprising a process for preparing the compound of Formula (II) comprising the steps of:

1) converting 3-hydroxybenzaldehyde to a compound of Formula (aa)

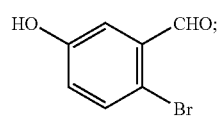

(aa)

2) treating the compound of Formula (aa) with itaconic acid to form a compound of Formula (bb):

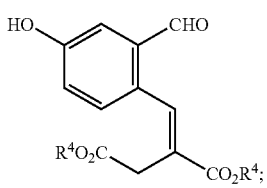

(bb)

3) converting the compound of Formula (bb) to a compound of Formula (cc)

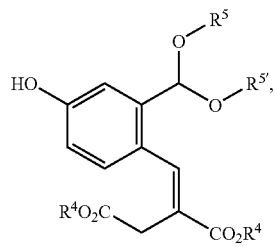
(cc)

where $R^5$ and $R^{5'}$ are $C_1$-$C_4$ alkyl or $R^5$ and $R^{5'}$, taken together with the atoms to which they are attached form a saturated 5- or 6-membered heterocyclic ring;

4) converting the compound of Formula (cc) to a compound of Formula (dd)

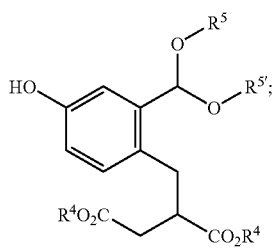
(dd)

5) converting the compound of Formula (dd) to a compound of Formula (ee)

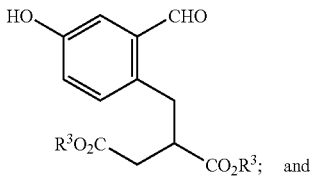
(ee)

6) converting the compound of Formula (ee) to a compound of Formula (II).

5. A process according to claim 2, further comprising a process for preparing the compound of Formula (II-S) comprising the steps of:

1) converting the compound having the formula:

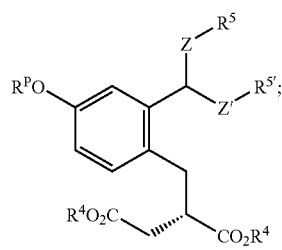

wherein $R^5$ and $R^{5'}$ are $C_1$-$C_4$ alkyl or $R^5$ and $R^{5'}$, taken together with the atoms to which they are attached form a saturated 5- or 6-membered heterocyclic ring and Z and Z' are independently selected from O, NH or NCH$_3$, to a compound having the formula:

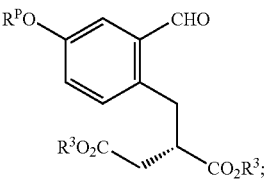

2) converting the compound formed in step 1) into a compound having the formula:

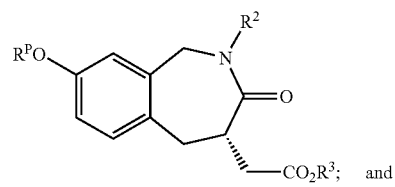

3) converting the compound formed in step 2) into the compound having the formula:

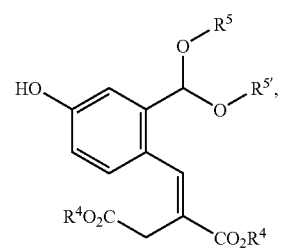
and 4) converting the compound formed in step 3) into the compound of Formula (II-S).

6. A process according to claim 2, further comprising a process for preparing the compound of Formula (II-S) comprising the steps of:

1) converting the compound having the formula:

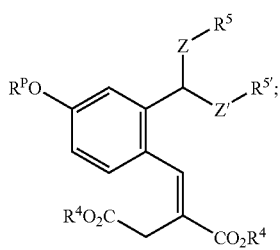

wherein $R^5$ and $R^{5'}$ are $C_1$-$C_4$ alkyl or $R^5$ and $R^{5'}$, taken together with the atoms to which they are attached form a saturated 5- or 6-membered heterocyclic ring, into a compound having the formula:

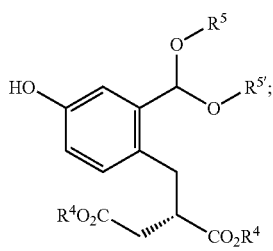

2) converting the compound formed in step 1) into a compound having the formula:

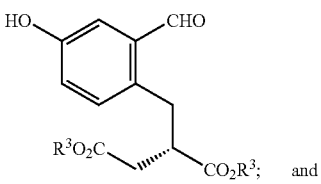

3) converting the compound formed in step 2) into the compound of Formula (II-S).

7. A process according to claim 1, further comprising a process for preparing the compound of Formula (I) having the formula:

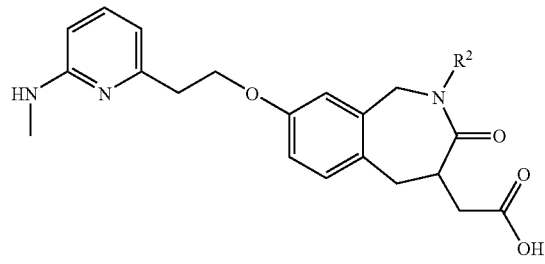

comprising the steps of:
1) converting 2-amino-6-methylpyridine into a compound having the formula:

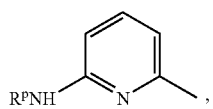

wherein $R^P$ is a suitable amino protecting group;
2) converting the compound formed in step 1) to a compound having the formula:

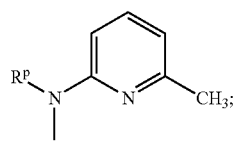

3) converting the compound formed in step 2) to a compound having the formula:

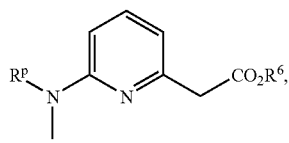

wherein $R^6$ is H or an alkyl carboxylic acid ester protecting group;
4) converting the compound formed in step 3) to a compound having the formula:

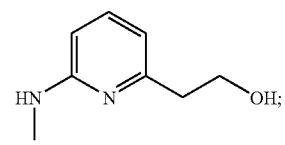

5) treating the compound formed in step 4) with a compound having the formula:

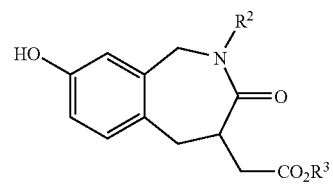

to form a compound having the formula:

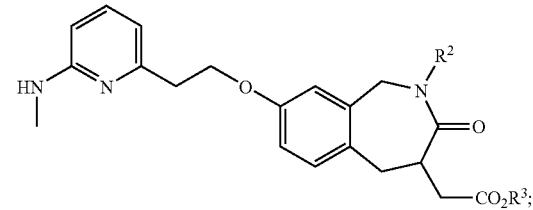

6) converting the compound formed in step 5) to the compound of Formula I.

8. A process according to claim 1, further comprising a process for preparing the compound of Formula (I) having the formula:

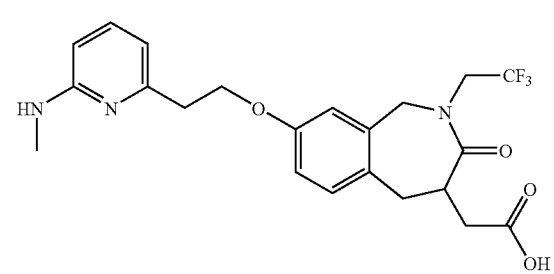

comprising the steps of:

1) converting 2-amino-6-methylpyridine into a compound having the Formula:

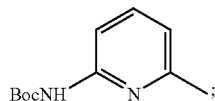

2) converting the compound formed in step 1) to a compound having the formula:

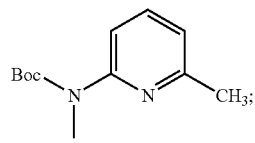

3) converting the compound formed in step 2) to a compound having the formula:

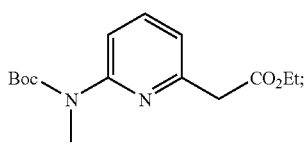

4) converting the compound formed in step 3) to a compound having the formula:

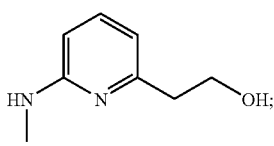

5) treating the compound formed in step 4) with a compound having the formula:

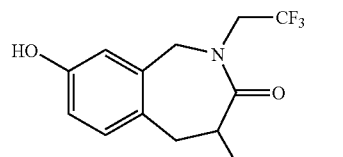

to form a compound having the formula:

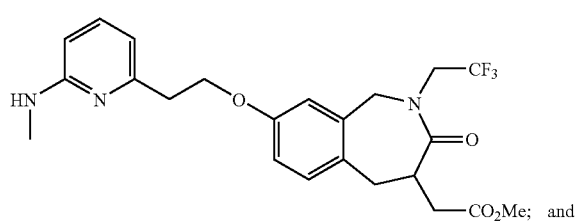

6) converting the compound formed in step 5) to the compound of Formula (I).

9. A process according to claim 1, further comprising a process for preparing the compound of Formula (I) having the formula:

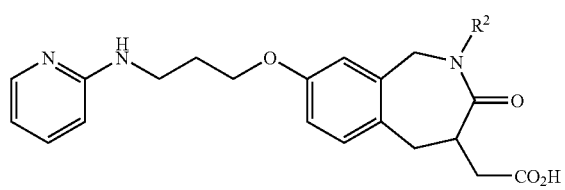

comprising the steps of:
1) converting a compound having the formula:

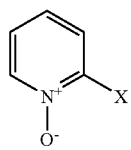

wherein X is halogen or —$OSO_2CF_3$, to a compound having the formula:

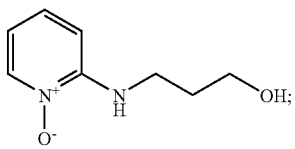

2) converting the compound formed in step 1) into a compound having the formula:

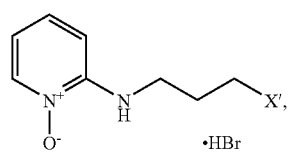

wherein X' is halogen, —$OSO_2CH_3$, —$OSO_2CF_3$, —$OSO_2$(phenyl), or —$OSO_2$(p-tolyl);

3) treating the compound formed in step 2) with a compound having the formula:

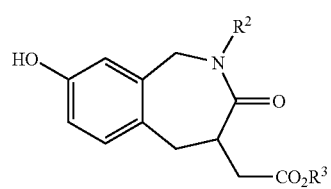

to form a compound having the formula:

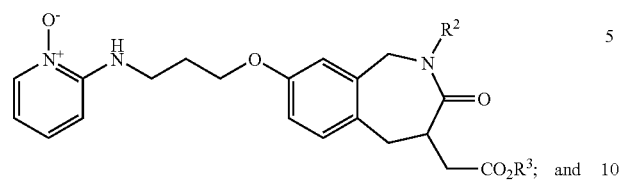

4) converting the compound formed in step 3) into the compound of Formula (I).

10. A process according to claim 1, further comprising a process for preparing the compound of Formula (I) having the formula:

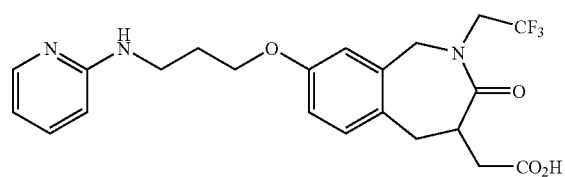

comprising the steps of:
1) converting 2-chloropyrdine, N-oxide to a compound having the formula:

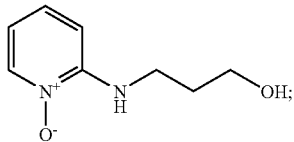

2) converting the compound formed in step 1) into a compound having the formula:

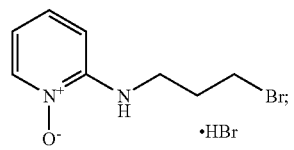

3) treating the compound formed in step 2) with a compound having the formula:

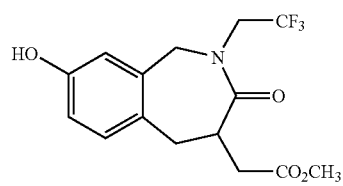

to form a compound having the formula:

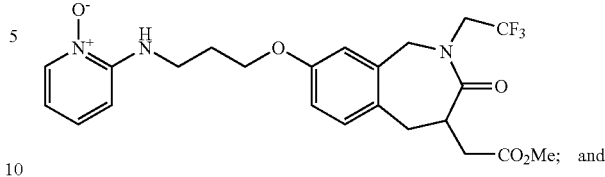

4) converting the compound formed in step 3) into the compound of Formula (I).

11. A process according to claim 1, wherein $R^3$ is H, $C_1$-$C_6$ alkyl or phenyl-$C_1$-$C_4$ alkyl-, wherein the phenyl moiety is unsubstituted or substituted by one or more substituents selected from ortho and para substituents selected from chloro, bromo, nitro, methoxy and methyl and $R^4$ is H, $C_1$-$C_6$ alkyl or phenyl-$C_1$-$C_4$ alkyl-, wherein the phenyl moiety is unsubstituted or substituted by one or more substituents selected from ortho and para substituents selected from chloro, bromo, nitro, methoxy and methyl.

12. A process according to claim 1, wherein $R^4$ is H or $C_1$-$C_4$ alkyl and $R^3$ is H or $C_1$-$C_4$ alkyl.

13. A process according to claim 1, wherein $R^4$ is H and $R^3$ is methyl.

14. A compound having the formula:

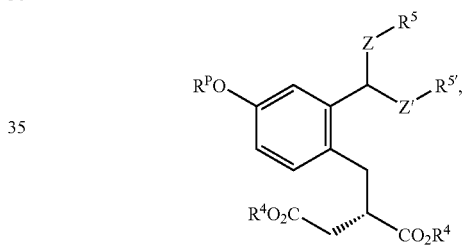

wherein:
$R^P$ is H or a suitable phenol protecting group;
$R^4$ is H or a carboxylic acid ester protecting group;
$R^5$ and $R^{5'}$ are $C_1$-$C_4$ alkyl or $R^5$ and $R^{5'}$, taken together with the atoms to which they are attached form a saturated 5- or 6-membered heterocyclic ring and Z and Z' are independently selected from O, NH or $NCH_3$;
or a pharmaceutically acceptable salt or solvate thereof.

15. A compound according to claim 14, wherein $R^4$ is H, $C_1$-$C_6$ alkyl or phenyl-$C_1$-$C_4$ alkyl-, wherein the phenyl moiety is unsubstituted or substituted by one or more substituents selected from ortho and para substituents selected from chloro, bromo, nitro, methoxy and methyl.

16. A compound according to claim 14, wherein $R^4$ is H, $R^P$ is H, Z and Z' are both O, and $R^5$ and $R^{5'}$ are methyl.

17. A compound having the formula:

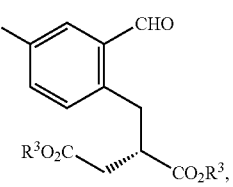

wherein:
R$^P$ is H or a suitable phenol protecting group;
R$^3$ is H or a carboxylic acid ester protecting group;
or a pharmaceutically acceptable salt or solvate thereof.

18. A compound according to claim 17, wherein R$^3$ is H, C$_1$-C$_6$ alkyl or phenyl-C$_1$-C$_4$ alkyl-, wherein the phenyl moiety is unsubstituted or substituted by one or more substituents selected from ortho and para substituents selected from chloro, bromo, nitro, methoxy and methyl.

19. A compound according to claim 17, wherein R$^P$ is H and R$^3$ is H or C$_1$-C$_4$ alkyl.

20. A compound:
2-[(2-formyl-4-hydroxyphenyl)methylidene]succinic acid, 2-carboxyl-4-[(2-formyldimethylacetal-4-hydroxyphenyl)]butyric acid, bis(dicyclohexylamine) salt,
(S)-2-carboxyl-4-[(2-formyldimethylacetal-4-hydroxyphenyl)]butyric acid, bis(dicyclohexylamine)salt,
dimethyl 2-[(2-formyl-4-hydroxyphenyl)methyl]butanedioate, and dimethyl(2S)-2-[(2-formyl-4-hydroxyphenyl)methyl]butanedioate.

* * * * *